(12) United States Patent
Fujita et al.

(10) Patent No.: US 12,420,233 B2
(45) Date of Patent: Sep. 23, 2025

(54) RAW MATERIAL LIQUID CONCENTRATION SYSTEM

(71) Applicant: Asahi Kasei Kabushiki Kaisha, Tokyo (JP)

(72) Inventors: Mitsuru Fujita, Tokyo (JP); Masato Mikawa, Tokyo (JP); Daisuke Hotta, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 798 days.

(21) Appl. No.: 17/614,085

(22) PCT Filed: May 29, 2020

(86) PCT No.: PCT/JP2020/021444
§ 371 (c)(1),
(2) Date: Nov. 24, 2021

(87) PCT Pub. No.: WO2020/241865
PCT Pub. Date: Dec. 3, 2020

(65) Prior Publication Data
US 2022/0226777 A1    Jul. 21, 2022

(30) Foreign Application Priority Data

May 31, 2019 (JP) ................................. 2019-102656
Mar. 9, 2020 (JP) ................................. 2020-040211

(51) Int. Cl.
| | |
|---|---|
| *B01D 61/02* | (2006.01) |
| *A61K 38/05* | (2006.01) |
| *B01D 61/00* | (2006.01) |
| *B01D 61/36* | (2006.01) |
| *B01D 63/04* | (2006.01) |
| *B01D 69/08* | (2006.01) |
| *B01D 69/10* | (2006.01) |
| *B01D 69/12* | (2006.01) |
| *B01D 71/68* | (2006.01) |

(52) U.S. Cl.
CPC ............ *B01D 61/002* (2013.01); *A61K 38/05* (2013.01); *B01D 61/364* (2013.01); *B01D 63/04* (2013.01); *B01D 69/08* (2013.01); *B01D 69/087* (2013.01); *B01D 69/10* (2013.01); *B01D 69/12* (2013.01); *B01D 69/1251* (2022.08); *B01D 71/68* (2013.01)

(58) Field of Classification Search
CPC .......... C07K 1/14; C07K 1/34; B01D 61/002; B01D 69/1251; B01D 61/364; B01D 63/04; B01D 69/08; B01D 69/087; B01D 69/10; B01D 69/12; B01D 71/68; A61K 38/05

See application file for complete search history.

(56) References Cited

U.S. PATENT DOCUMENTS

| | | | |
|---|---|---|---|
| 2012/0273417 A1 | 11/2012 | McGinnis et al. | |
| 2016/0016127 A1* | 1/2016 | Mentzel | B01D 69/144 |
| | | | 210/257.2 |
| 2017/0028349 A1* | 2/2017 | Blandin | B01D 61/027 |
| 2017/0225131 A1 | 8/2017 | Morita et al. | |
| 2017/0266625 A1 | 9/2017 | Kiguchi et al. | |
| 2019/0009218 A1* | 1/2019 | Choong | B01D 61/0021 |
| 2020/0353415 A1 | 11/2020 | Fujita et al. | |
| 2021/0339194 A1 | 11/2021 | Hotta et al. | |

FOREIGN PATENT DOCUMENTS

| | | |
|---|---|---|
| EP | 2674211 A1 | 12/2013 |
| JP | H11-075759 A | 3/1999 |
| JP | 2011-525147 A | 9/2011 |
| JP | 2013-509295 A | 3/2013 |
| JP | 2016-155078 A | 9/2016 |
| JP | 2017-136587 A | 8/2017 |
| JP | 2017-205740 A | 11/2017 |
| WO | 2009/155596 A2 | 12/2009 |
| WO | 2011/059751 A2 | 5/2011 |

(Continued)

OTHER PUBLICATIONS

International Search Report issued in corresponding International Patent Application No. PCT/JP2020/021444 dated Jun. 30, 2020.
International Preliminary Report on Patentability and Written Opinion issued in corresponding International Patent Application No. PCT/JP2020/021444 dated Dec. 9, 2021.
Supplementary European Search Report issued in corresponding European Patent Application No. 20814976.5 dated Jun. 22, 2022.
Wang et al., "Integrated forward osmosis membrane distillation (FO-MD) hybrid system for the concentration of protein solutions," Chemical Engineering Science, 66 (11): 2421-2430 (2011).
Wang et al., "Polybenzimidazole (PBI) nanofiltration hollow fiber membranes applied in forward osmosis process," Journal of Membrane Science, 300 (1-2): 6-12 (2007).

(Continued)

*Primary Examiner* — Catherine S Hibbert
(74) *Attorney, Agent, or Firm* — Morgan, Lewis & Bockius LLP

(57) ABSTRACT

Provided is a system preventing or reducing adhesion of a raw material component to a membrane surface and increasing the recovery rate of the raw material component after concentration. A raw material liquid concentration system for a medicine production process comprising a forward osmosis membrane unit having a forward osmosis membrane, and a raw material liquid side space and an inductive solution side space which are separated from each other by the forward osmosis membrane; a raw material liquid channel supplying, to the raw material liquid side space, a raw material liquid containing a solvent and a solute; an inductive solution channel supplying, to the inductive solution side space, an inductive solution containing an inductive material; a concentrated liquid channel removing a concentrated raw material liquid from the forward osmosis membrane unit; and a diluted inductive solution channel removing a diluted inductive solution from the forward osmosis membrane unit.

13 Claims, 3 Drawing Sheets

(56) References Cited

FOREIGN PATENT DOCUMENTS

| WO | 2013/036111 A1 | 3/2013 |
|---|---|---|
| WO | 2013/170977 A1 | 11/2013 |
| WO | 2016/024573 A1 | 2/2016 |
| WO | 2016/027869 A1 | 2/2016 |
| WO | 2019/016699 A1 | 1/2019 |
| WO | 2019/098390 A1 | 5/2019 |
| WO | 2020/050282 A1 | 3/2020 |

* cited by examiner

RAW MATERIAL LIQUID CONCENTRATION SYSTEM

FIELD

The present invention relates to a raw material liquid concentration system for a pharmaceutical production process. Specifically, the present invention relates to a raw material liquid concentration system which can efficiently concentrate a raw material liquid while suppressing deterioration and reduction of components in the raw material liquid by separating a portion of the solvent from the raw material liquid, which is used for pharmaceutical purposes, by the forward osmosis method to concentrate the raw material liquid.

BACKGROUND

Proteins such as enzymes and peptides are widely used as diagnostic/testing agents and pharmaceuticals. Since these raw materials are very expensive, it is important to recover them at a high yield without denaturation in the production process.

Ultrafiltration membranes are commonly used as one method for stably and efficiently extracting and purifying proteins. Ultrafiltration membranes are a technology in which separation is carried out by sieving, and which can reduce the energy load, since temperature changes are not involved. For example, proteins having a molecular weight of several thousand to several million are often fractionally purified with an ultrafiltration membrane. Although components larger than the molecular weight cut-off of the membrane are retained, water passes through the membrane, which is effective for protein concentration (for example, Patent Literature 1).

Furthermore, the reverse osmosis (RO) method, in which a membrane which allows a solvent to permeate at the molecular level is used, is known. The RO method is a method in which a raw material liquid is concentrated by increasing the pressure of a raw material liquid to a predetermined pressure higher than the osmotic pressure of the raw material liquid, supplying the raw material liquid to an RO membrane module, whereby the raw material liquid permeates the RO membrane and the solvent (typically water) in the raw material liquid is removed (for example, Patent Literature 2).

CITATION LIST

Patent Literature

[PTL 1] WO 2013/170977
[PTL 2] Japanese Unexamined Patent Publication (Kokai) No. 11-75759

Summary

Technical Problem

However, in Patent Literature 1, since the ultrafiltration membrane requires pressurization of the raw material liquid, the solute contained in the raw material liquid adheres to the membrane surface, and there is a problem in that the recovery rate is reduced. Furthermore, in the case of medium-molecular-weight pharmaceuticals, which are currently in development, some have a molecular weight smaller than the molecular weight cut-off of the ultrafiltration membrane, whereby the recovery rate is reduced because a portion thereof permeates the ultrafiltration membrane.

In Patent Literature 2, since pressurization is required, the solute contained in the raw material liquid adheres to the surface of the RO membrane, which brings about a problem in that the recovery rate is reduced.

The present invention aims to provide a raw material liquid concentration system and a raw material liquid concentration method with which the adhesion of raw material components to the membrane surface can be suppressed and the recovery rate of the concentrated raw material components (more specifically, the solute in the raw material liquid) can be increased.

Solution to Problem

Examples of the modes for carrying out the present invention are as follows.

[1] A raw material liquid concentration system for a pharmaceutical production process, the system comprising:
  a forward osmosis membrane unit having a forward osmosis membrane and a raw material liquid-side space and a draw solution-side space which are separated from each other by the forward osmosis membrane,
  a raw material liquid flow path for supplying a raw material liquid containing a solvent and a solute to the raw material liquid-side space,
  a draw solution flow path for supplying a draw solution containing a draw substance to the draw solution-side space,
  a concentrate flow path for discharging a concentrated raw material liquid from the forward osmosis membrane unit, and
  a diluted draw solution flow path for discharging a diluted draw solution from the forward osmosis membrane unit, wherein
  the forward osmosis membrane moves the solvent in the raw material liquid into the draw solution and moves the draw substance in the draw solution into the raw material liquid to generate a concentrated raw material liquid and a diluted draw solution.

[2] The raw material liquid concentration system according to Aspect 1, wherein the forward osmosis membrane is a hollow fiber membrane.

[3] The raw material liquid concentration system according to Aspect 2, wherein
  a plurality of the hollow fiber membranes form a hollow-fiber fiber bundle,
  the hollow fiber membranes each comprise a microporous support membrane and a separation active layer, which is a polymer thin film provided on an inner surface of the microporous support membrane,
  a membrane area of the hollow-fiber fiber bundle is 0.01 m$^2$ or more, and
  a coefficient of variation of a thickness of the separation active layer in the radial direction and the longitudinal direction of the hollow-fiber fiber bundle in a scanning electron microscope image in which a thickness-direction cross-section of the separation active layer is captured, is 0 to 60%.

[4] The raw material liquid concentration system according to Aspect 2 or 3, wherein a pressure of 10 kPa to 200 kPa is exerted from an interior toward an exterior of the hollow fiber membrane.

[5] The raw material liquid concentration system according to any one of Aspects 1 to 4, which is a cross-flow filtration system.

[6] The raw material liquid concentration system according to any one of Aspects 1 to 5, further comprising a raw material liquid temperature adjustment mechanism.

[7] The raw material liquid concentration system according to any one of Aspects 1 to 6, further comprising a first draw solution regeneration unit which removes the solvent from the diluted draw solution to obtain a regenerated draw solution and which again supplies the obtained regenerated draw solution as the draw solution.

[8] The raw material liquid concentration system according to Aspect 7, wherein the first draw solution regeneration unit is an evaporator.

[9] The raw material liquid concentration system according to any one of Aspects 1 to 8, further comprising a second draw solution regeneration unit which removes the solvent from the draw solution to obtain a concentrated draw solution and which supplies a mixture of the obtained concentrated draw solution and the diluted draw solution as the draw solution.

[10] The raw material liquid concentration system according to Aspect 9, wherein the second draw solution regeneration unit is an evaporator.

[11] The raw material liquid concentration system according to any one of Aspects 1 to 10, wherein the forward osmosis membrane is a membrane having a thin film layer composed of at least one selected from the group consisting of polyethersulfone, polysulfone, polyketone, polyetheretherketone, polyphenylene ether, polyvinylidene fluoride, polyacrylonitrile, polyimine, polyimide, polybenzoxazole, polybenzimidazole, sulfonated tetrafluoroethylene, and polyamide as a primary component.

[12] The raw material liquid concentration system according to any one of Aspects 1 to 11, further comprising:
a raw material liquid to be supplied to the raw material liquid-side space via the raw material liquid flow path, and
a draw solution to be supplied to the draw solution-side space via the draw solution flow path.

[13] The raw material liquid concentration system according to Aspect 12, wherein a ratio (permeation flux of the draw substance/permeation flux of the solvent) of a permeation flux of the draw substance, by which the draw substance in the draw solution is moved into the raw material liquid, to a permeation flux of the solvent, by which the solvent in the raw material liquid is moved into the draw solution, is 3 or less.

[14] The raw material liquid concentration system according to Aspect 12 or 13, wherein a ratio (permeation flux of the draw substance/permeation flux of the solvent) of a permeation flux of the draw substance, by which the draw substance in the draw solution is moved into the raw material liquid, to a permeation flux of the solvent, by which the solvent in the raw material liquid is moved into the draw solution, is 0.001 to 1.

[15] The raw material liquid concentration system according to any one of Aspects 12 to 14, wherein the solvent is composed of water, acetic acid, acetonitrile, methanol, 2-propanol or a mixture thereof as a primary component.

[16] The raw material liquid concentration system according to any one of Aspects 12 to 15, wherein the concentrated raw material liquid is circulated at a circulation linear velocity of 0.03 cm/s to 15 cm/s.

[17] The raw material liquid concentration system according to any one of Aspects 12 to 16, wherein an initial permeation flux of the forward osmosis membrane is 0.1 L/(m²×hr) to 50 L/(m²×hr).

[18] The raw material liquid concentration system according to any one of Aspects 12 to 17, wherein the concentrated raw material liquid contains at least one selected from the group consisting of nucleic acids, oligopeptides, amino acids, antibiotics, small molecule pharmaceuticals, and vitamins.

[19] The raw material liquid concentration system according to any one of Aspects 12 to 18, wherein the solute comprises a compound having a number average molecular weight of 100 to 6000.

[20] The raw material liquid concentration system according to any one of Aspects 12 to 19, wherein the draw solution contains an inorganic salt.

[21] A raw material liquid concentration method for a pharmaceutical production process, the method comprising:
a first step wherein a raw material liquid containing a solvent and a solute and a draw solution containing a draw substance are contacted via a forward osmosis membrane to move the solvent in the raw material liquid into the draw solution and move the draw substance in the draw solution into the raw material liquid to obtain a concentrated raw material liquid and a diluted draw solution.

[22] The raw material liquid concentration method according to Aspect 21, wherein the forward osmosis membrane is a hollow fiber membrane.

[23] The raw material liquid concentration method according to Aspect 22, wherein
a plurality of the hollow fiber membranes form a hollow-fiber fiber bundle,
the hollow fiber membranes each comprise a microporous support membrane and a separation active layer, which is a polymer thin film provided on an inner surface of the microporous support membrane,
a membrane area of the hollow-fiber fiber bundle is 0.01 m² or more, and
a coefficient of variation of a thickness of the separation active layer in the radial direction and the longitudinal direction of the hollow-fiber fiber bundle in a scanning electron microscope image in which a thickness-direction cross-section of the separation active layer is captured, is 0 to 60%.

[24] The raw material liquid concentration method according to Aspect 22 or 23, wherein in the first step, a pressure of 10 kPa to 200 kPa is exerted from an interior toward an exterior of the hollow fiber membrane.

[25] The raw material liquid concentration method according to any one of Aspects 21 to 24, wherein the first step is carried out by cross-flow filtration.

[26] The raw material liquid concentration method according to any one of Aspects 21 to 25, wherein in the first step, the temperature of the raw material liquid is adjusted to the range of 5° C. to 50° C.

[27] The raw material liquid concentration method according to any one of Aspects 21 to 26, further having a first draw solution regeneration step wherein the solvent is removed from the diluted draw solution to obtain a regenerated draw solution and the obtained regenerated draw solution is used again as the draw solution.

[28] The raw material liquid concentration method according to Aspect 27, wherein removal of the solvent from the diluted draw solution in the first draw solution regeneration step is carried out by an evaporation means.

[29] The raw material liquid concentration method according to any one of Aspects 21 to 28, further having a second draw solution regeneration step wherein the solvent is removed from the draw solution to obtain a concentrated draw solution and a mixture of the obtained concentrated draw solution and the diluted draw solution is used as the draw solution.

[30] The raw material liquid concentration method according to Aspect 29, wherein removal of the solvent from the draw solution in the second draw solution regeneration step is carried out by an evaporation means.

[31] The raw material liquid concentration method according to any one of Aspects 21 to 30, wherein the forward osmosis membrane is a membrane having a thin film layer composed of at least one selected from the group consisting of polyethersulfone, polysulfone, polyketone, polyetheretherketone, polyphenylene ether, polyvinylidene fluoride, polyacrylonitrile, polyimine, polyimide, polybenzoxazole, polybenzimidazole, sulfonated tetrafluoroethylene, and polyamide as primary components.

The raw material liquid concentration method according to any one of Aspects 21 to 31, wherein a ratio (permeation flux of the draw substance [g/(m$^2$×hr)]/permeation flux of the solvent [L/(m$^2$×hr)]) of a permeation flux of the draw substance, by which the draw substance in the draw solution is moved into the raw material liquid, to a permeation flux of the solvent, by which the solvent in the raw material liquid is moved into the draw solution, in the first step is 3 [g/L] or less. [33] The raw material liquid concentration method according to any one of Aspects 21 to 32, wherein a ratio (permeation flux of the draw substance [g/(m$^2$×hr)]/permeation flux of the solvent [L/(m$^2$×hr)]) of a permeation flux of the draw substance, by which the draw substance in the draw solution is moved into the raw material liquid, to a permeation flux of the solvent, by which the solvent in the raw material liquid is moved into the draw solution, in the first step is 0.001 to 1 [g/L].

[34] The raw material liquid concentration method according to any one of Aspects 21 to 33, wherein the solvent is composed of water, acetic acid, acetonitrile, methanol, 2-propanol or a mixture thereof as a primary component.

[35] The raw material liquid concentration method according to any one of Aspects 21 to 34, wherein in the first step, the concentrated raw material liquid is circulated at a circulation linear velocity of 0.03 cm/s to 15 cm/s.

[36] The raw material liquid concentration method according to any one of Aspects 21 to 35, wherein in the first step, an initial permeation flux of the forward osmosis membrane is 0.1 L/(m$^2$×hr) to 50 L/(m$^2$×hr).

[37] The raw material liquid concentration method according to any one of Aspects 21 to 36, wherein the pharmaceutical production process is a process for the production of at least one selected from the group consisting of nucleic acids, oligopeptides, amino acids, antibiotics, small molecule pharmaceuticals, and vitamins.

[38] The raw material liquid concentration method according to any one of Aspects 21 to 37, wherein the solute comprises a compound having a number average molecular weight of 100 to 6000.

[39] The raw material liquid concentration method according to any one of Aspects 21 to 38, wherein the draw solution comprises a solution containing an inorganic salt.

Advantageous Effects of Invention

According to an aspect of the present invention, there is provided a raw material liquid concentration system and a raw material liquid concentration method with which the adhesion of raw material components to the membrane surface can be suppressed and the recovery rate of the concentrated raw material components (more specifically, the solute in the raw material liquid) can be increased.

DESCRIPTION OF EMBODIMENTS

Figure 1:
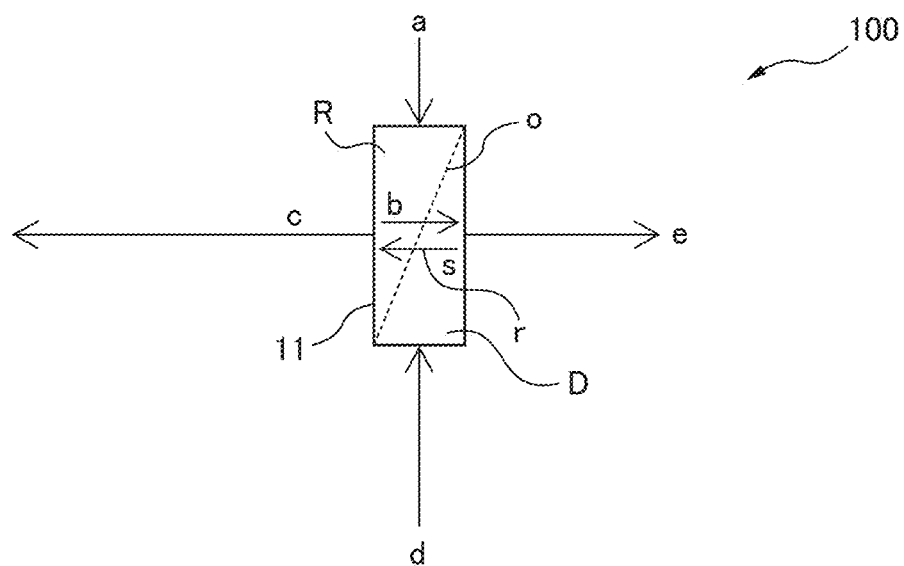
FIG. 1 is a conceptual diagram detailing an example of an embodiment of the raw material liquid concentration system of the present invention.

The embodiment (hereinafter referred to as the present embodiment) of the present invention will be described in detail below a as non-limiting example.

An aspect of the present invention provides a raw material liquid concentration system for a pharmaceutical process and a raw material liquid concentration method. according to this system and method, useful components which are sensitive to heat or pressure can be concentrated by heating or pressurization without denaturation. Furthermore, when concentrating the raw material liquid with a forward osmosis membrane, by permeating the solute of the draw solution to the raw material liquid side at an appropriate flow velocity and supplying the raw material liquid to the forward osmosis membrane at an appropriate linear velocity, adhesion of the raw material components to the surface of the forward osmosis membrane can be suppressed, and the recovery rate of the concentrated raw material component (more specifically, the solute in the raw material liquid) can be increased.

«Raw Material Liquid Concentration System»

One aspect of the present invention provides a raw material liquid concentration system for a pharmaceutical production process. In this aspect, the raw material liquid concentration system comprises:

a forward osmosis membrane unit having a forward osmosis membrane and a raw material liquid-side space and a draw solution-side space which are separated from each other by the forward osmosis membrane, a raw material liquid flow path for supplying a raw material liquid containing a solvent and a solute to the raw material liquid-side space, a draw solution flow path for supplying a draw solution containing a draw substance to the draw solution-side space, a concentrate flow path for discharging a concentrated raw material liquid from the forward osmosis membrane unit, and a diluted draw solution flow path for discharging a diluted draw solution from the forward osmosis membrane unit. In this aspect, the forward osmosis membrane moves the solvent in the raw material liquid into the draw solution and moves the draw substance in the draw solution into the raw material liquid to generate a concentrated raw material liquid and a diluted draw solution.

In one aspect, the raw material liquid concentration system further comprises a raw material liquid to be supplied to the raw material liquid-side space via the raw material liquid flow path and a draw solution to be supplied to the draw solution-side space via the draw solution flow path.

The ratio (permeation flux of the draw substance/permeation flux of the solvent) of the permeation flux of the draw substance, by which the draw substance in the draw solution is moved into the raw material liquid, to a permeation flux of the solvent, by which the solvent in the raw material liquid is moved into the draw solution, is preferably 3 or less, more preferably 1 or less, and preferably 0.001 or more.

An overview of the raw material liquid concentration system of the present embodiment will be describe with reference to the drawings as needed.

FIG. 1 is a conceptual diagram detailing an example of an embodiment of the raw material liquid concentration system of the present invention. Referring to FIG. 1, the raw material liquid concentration unit 100 comprises a forward osmosis membrane o and a forward osmosis membrane unit 11 having a raw material liquid-side space R and a draw solution-side space D which are separated from each other by the forward osmosis membrane o. In the forward osmosis membrane unit 11, the raw material liquid and the draw solution are contacted via the forward osmosis membrane to move the solvent in the raw material liquid into the draw solution, whereby concentration of the raw material liquid is carried out, and the draw solution is diluted to obtain a concentrated raw material liquid and a diluted draw solution.

Referring to FIG. 1, the interior space of the forward osmosis membrane unit 11 is divided into two parts, the raw material liquid-side space R and the draw solution-side space D, by the forward osmosis membrane o. The raw material liquid a, which is the target of concentration, is introduced into the raw material liquid-side space R of the forward osmosis membrane unit. Conversely, the draw solution d is introduced into the draw solution-side space D of the forward osmosis membrane unit.

The raw material liquid a contains a solute and a solvent b. The draw solution d preferably contains a draw substance s and further contains the solvent b. The osmotic pressure of the draw solution d is set so as to be higher than that of the raw material liquid a.

Further, when the raw material liquid a and the draw solution d are contacted via the forward osmosis membrane o, using the osmotic pressure difference between the solutions as a driving force, the solvent b in the raw material liquid a passes through the forward osmosis membrane o and moves to the draw solution d side. As a result, a concentrated raw material liquid (raw material liquid which has been concentrated) c and a diluted draw solution (draw solution which has been diluted) e are obtained.

The raw material liquid concentration system of the present embodiment may employ a total amount filtration system or a cross-flow filtration system. From the viewpoint of filtration flow velocity and suppression of membrane contamination, the cross-flow filtration system is preferable. The forward osmosis membrane unit 11 of FIG. 1 illustrates an example in which the raw material liquid a and the draw solution d counter-flow, but they may flow in parallel.

Figure 2:
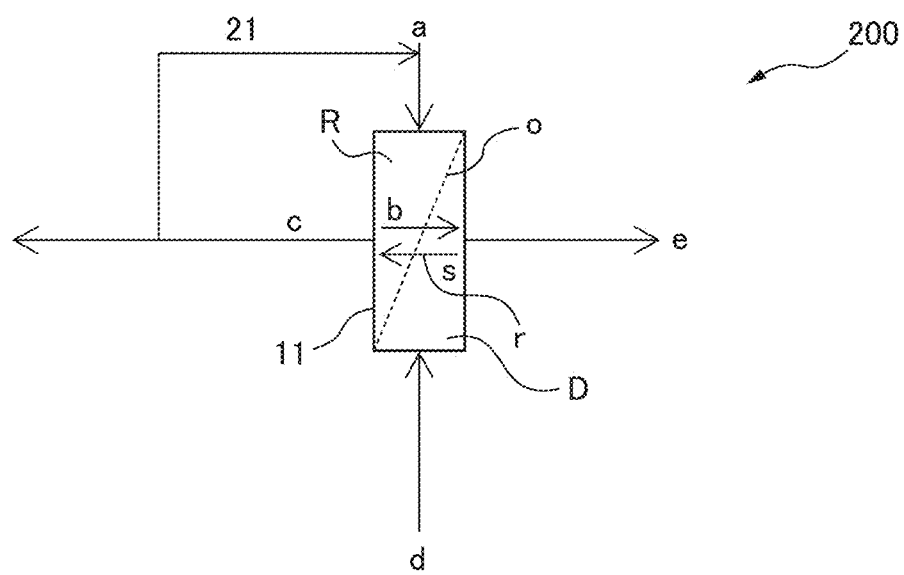
FIG. 2 is a conceptual diagram detailing another example of an embodiment of the raw material liquid concentration system of the present invention.

FIG. 2 is a conceptual diagram detailing another example of the embodiment of the raw material liquid concentration system of the present invention. Referring to FIG. 2, the raw material liquid concentration system 200 is identical to the raw material liquid concentration system 100 shown in FIG. 1 except that it further comprises a circulation mechanism 21 for reusing the concentrated raw material liquid as the raw material liquid. The number of times the raw material liquid a passes through the circulation mechanism 21 (i.e., the number of times the concentrated raw material liquid obtained in the forward osmosis membrane unit is reused as the raw material liquid in the forward osmosis membrane unit) is arbitrary.

When the concentrated raw material liquid is circulated in the circulation mechanism, the linear velocity thereof is preferably 0.03 cm/s to 15 cm/s.

Figure 3:
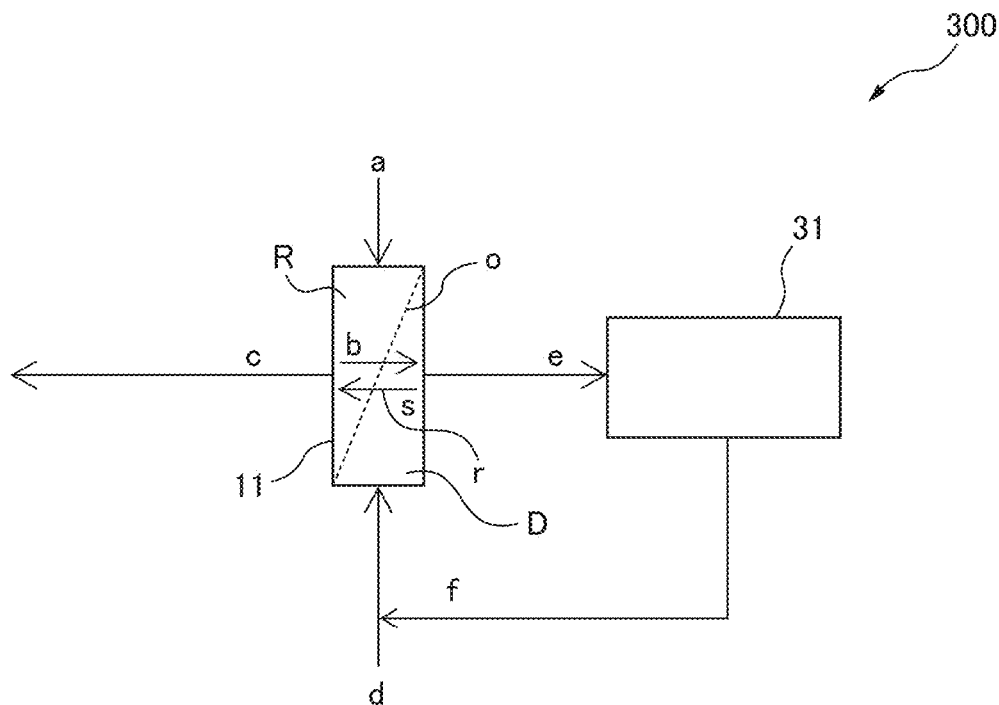
FIG. 3 is a conceptual diagram detailing yet another example of an embodiment of the raw material liquid concentration system of the present invention.

FIG. 3 is a conceptual diagram detailing yet another example of the embodiment of the raw material liquid concentration system. Referring to FIG. 3, the raw material liquid concentration system 300 is identical to the raw material liquid concentration system 100 shown in FIG. 1 except that it further comprises a first draw solution regeneration unit 31. The first draw solution regeneration unit may have a structure such that the diluted draw solution e is concentrated by removing the solvent b therefrom to obtain a regenerated draw solution f, and the obtained regenerated draw solution f is again circulated as the draw solution d. The removal of the solvent b from the diluted draw solution e by the first draw solution regeneration unit 31 may be carried out by a known concentration device, such as an evaporator.

Note that the regenerated draw solution f may contain a part of the solvent b. For example, when the solvent b is a multi-component system containing water and contains an azeotropic component, it is difficult to remove the solvent b. Thus, the regenerated draw solution f contains a part of the solvent b, but this does not pose a problem in the system.

Figure 4:
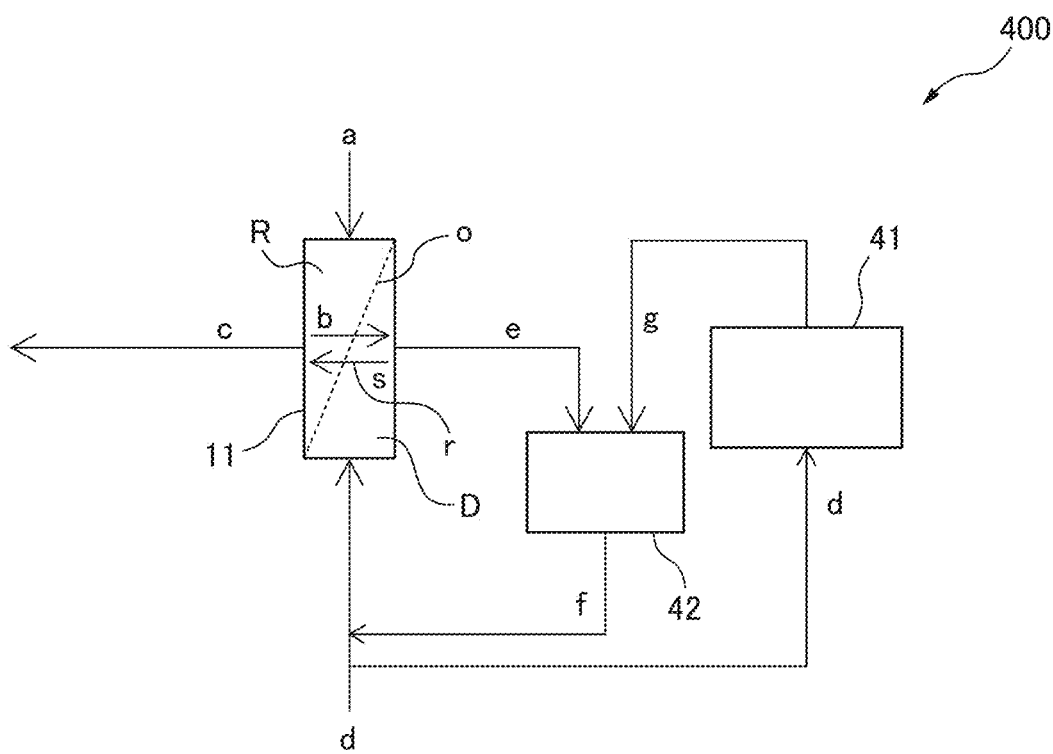
FIG. 4 is a conceptual diagram detailing yet another example of an embodiment of the raw material liquid concentration system of the present invention.

FIG. 4 is a conceptual diagram detailing yet another example of the embodiment of the raw material liquid concentration system of the present invention. Referring to FIG. 4, the raw material liquid concentration system 400 is identical to the raw material liquid concentration system 300 shown in FIG. 3 except that it further comprises a second draw solution regeneration unit 41 and a mixing unit 42 instead of the first draw solution regeneration until 31. The raw material liquid concentration system 400 may have a structure such that the solvent b is removed from the draw solution d to obtain a concentrated draw solution g in the second draw solution regeneration unit 41, and the obtained concentrated draw solution g and the diluted draw solution e are mixed in the mixing unit 42 to generate a mixture (regenerated draw solution f), and the regenerated draw solution f is used as the draw solution d. The removal of the solvent b from the draw solution d by the second draw solution regeneration unit 41 may be carried out by a known concentration device such as an evaporator. The mixing unit 42 may be, for example, a buffer tank.

Note that a part of the solvent b may be included in the concentrated draw solution g. For example, when the solvent b is a multi-component system containing water and contains an azeotropic component, it is difficult to remove the solvent b. Thus, the concentrated draw solution g contains a part of the solvent b, but this does not pose a problem in the system.

Figure 5:
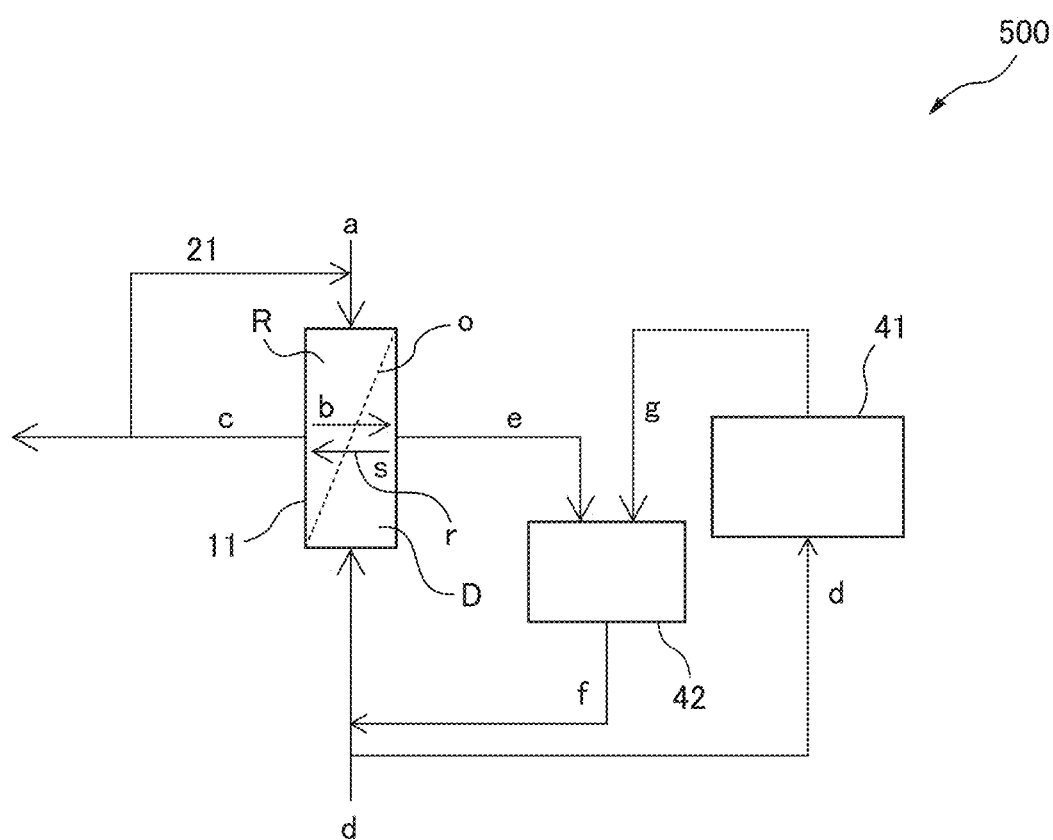
FIG. 5 is a conceptual diagram detailing yet another example of an embodiment of the raw material liquid concentration system of the present invention.

FIG. 5 is a conceptual diagram detailing yet another example of the embodiment of the raw material liquid concentration system of the present invention. Referring to FIG. 5, the raw material liquid concentration system 500 is identical to the raw material liquid concentration system 400 shown in FIG. 4 except that it further comprises the circulation mechanism 21 shown in FIG. 2. Note that in FIG. 5, an example in which the second draw solution regeneration unit 41 is used is shown, but in place or in addition thereto, the first draw solution regeneration unit 31 shown in FIG. 3 may be used.

Suitable examples of the components constituting the raw material liquid concentration system will be described below.

<Raw Material Liquid a>

The raw material liquid a is a fluid containing a solute and the solvent b and is intended to be concentrated by the raw material liquid concentration system of the present embodiment. The raw material liquid a may be an emulsion as long as it is a fluid. In a typical aspect, the raw material liquid is housed in a raw material liquid tank and is supplied to the forward osmosis membrane unit via the raw material liquid flow path.

In the raw material liquid concentration system of the present embodiment, a concentrate from which the solvent has been removed can be obtained while maintaining the composition of the raw material liquid a substantially as-is. Thus, when the raw material liquid concentration system of the present embodiment is applied to concentration of a pharmaceutical or raw material thereof, the concentration can be carried out while maintaining pharmaceutical efficacy. The raw material liquid a used in the present embodiment is a pharmaceutical product or raw material thereof. Specifically, one aspect of the present invention relates to a raw material liquid concentration system for a pharmaceutical production process.

The raw material liquid used in the raw material liquid concentration system of the present invention, which can be used as a pharmaceutical raw material, and the concentrated raw material liquid to be obtained therefrom each preferably contain at least one selected from the group consisting of nucleic acids, oligopeptides, amino acids, antibiotics, small molecule pharmaceuticals, and vitamins as the solute.

The solute contained in the raw material liquid preferably contains a compound having a number average molecular weight of 100 to 6000. The number average molecular weight of this compound is more preferably 200 to 5000. As long as the number average molecular weight is 100 or more, permeation through the forward osmosis membrane is impeded, and as long as the number average molecular weight is 6000 or less, adhesion of the raw material components to the surface of the forward osmosis membrane is unlikely to occur. Among these, the raw material liquid of the present embodiment preferably contains an oligopeptide because of the low affinity thereof with the forward osmosis membrane.

The above number average molecular weight is a value measured in terms of standard polyethylene oxide using gel permeation chromatography.

Examples of nucleic acids that can be concentrated in the raw material liquid concentration system of the present embodiment include oligonucleotides, RNA, aptamers, and decoys.

Examples of oligopeptides which can be concentrated in the raw material liquid concentration system of the present embodiment include L-alanyl-L-glutamine, β-alanyl-L-histidine cyclosporine, and glutathione. "Oligopeptide" as used herein refers to a compound in which an arbitrary amino acid having two to 50 residues is bound. The oligopeptide may be chained or cyclic.

Examples of amino acids which can be concentrated in the raw material liquid concentration system of the present embodiment include essential amino acids (for example, tryptophan, lysine, methionine, phenylalanine, threonine, valine, leucine, and isoleucine), non-essential amino acids (for example, arginine, glycine, alanine, serine, tyrosine, cysteine, aspartic acid, glutamine, proline, aspartic acid, and glutamic acid), and non-natural amino acids. "Non-natural amino acids" refers to any non-naturally occurring artificial compound having an amino acid skeleton in the molecule thereof, and can be produced by binding various labeled compounds to an amino acid skeleton. The "amino acid skeleton" includes a carboxyl group, an amino group, and a portion connecting these groups in an amino acid. The "labeled compounds" include dye compounds, fluorescent substances, chemical/bioluminescent substances, enzyme substrates, coenzymes, antigenic substances, and protein binding substances which are known to a person skilled in the art.

Examples of non-natural amino acid include "labeled amino acids", which are amino acids which are bound to a labeled compound. Examples of labeled amino acids include amino acids in which a labeled compound is bound to an amino acid having an amino acid skeleton containing an aromatic ring such as a benzene ring in the side chain thereof. Furthermore, examples thereof include non-natural amino acids to which a specific function is imparted, for example, photoresponsive amino acids, photoswitch amino acids, fluorescent probe amino acids, and fluorescently-labeled amino acids.

Examples of antibiotics that can be concentrated in the raw material liquid concentration system of the present embodiment include streptomycin and vancomycin.

The number average molecular weight of the solution containing the small molecule pharmaceutical is 1000 or less, and particularly preferably 100 to 1000. Examples of small molecule pharmaceuticals which can be concentrated in the raw material liquid concentration system of the present embodiment include various anticancer agents, small molecule pharmaceutical compounds which serves as a substrate for gastrointestinal excretion transporters such as P-gp or BCRP, therapeutic agents for osteoporosis and Paget's disease of bone such as sodium risedronate, and antiviral agents such as oseltamivir and zanamivir.

Examples of anticancer agents include alkylating agents, antimetabolites, microtubule inhibitors, antibiotic anticancer agents, topoisomerase inhibitors, platinum preparations, and hormonal agents. Examples of alkylating agents include cyclophosphamide, ifosfamide, nitrosourea, dacarbazine, temozolomide, nimustine, busulfan, melphalan, procarbazine, ranimustine. Examples of antimetabolites include enocitabine, carmofur, capecitabine, tegafur, gemcitabine, cytarabine, cytarabine ocphosphat, nerarabine, fluorouracil, fludarabin, pemetrexed, pentostatin, methotrexate, gradribine, doxifluridine, and hydroxycarbamide. Examples of microtubule inhibitors include alkaloid anticancer agents such as vincristine and taxane anticancer agents such as docetaxel and paclitaxel, and examples of antibiotic anticancer agents include mitomycin C, doxorubicin, epirubicin, daunorubicin, bleomycin, actinomycin D, acralubicin, idarubicin, pirarubicin, peplomycin, mitoxantrone, amurubicin, and dinostatin stimalamar. Examples of topoisomerase inhibitors include CPT-11 having a topoisomerase I inhibitory action, irinotecan, nogitecan, and etoposide and sobzoxane having a topoisomerase II inhibitory action. Examples of platinum preparations include cisplatin, nedabratin, oxaliplatin, and carboplatin. Examples of hormonal agents include dexamethasone, finasteride, and tamoxifen.

Examples of vitamins which can be concentrated in the raw material liquid concentration system of the present embodiment include vitamin A and derivatives and salts thereof, vitamins B such as vitamin B6 and vitamin B12 and derivatives and salts thereof, and vitamin C and derivatives and salts thereof.

<Draw Solution d>

The draw solution d contains a draw substance and preferably further contains a solvent b. The draw solution d is a fluid which has a higher osmotic pressure than the raw material liquid a and which does not significantly denature the forward osmosis membrane o. In a typical embodiment, the draw solution is housed in a draw solution tank and supplied to the forward osmosis membrane unit via the draw solution flow path.

(Draw Substance)

Examples of draw substances that can be used in the present embodiment include salts, sugars, alcohols, and polymers. Thus, the draw solution of the present embodiment may be a solution containing one or more selected from salts, sugars, alcohols, and polymers. Thereamong, the draw solution of the present embodiment preferably contains an inorganic salt as the salt because it has a high osmotic pressure.

Examples of inorganic salts include naturally-occurring sodium chloride, potassium chloride, magnesium chloride, calcium chloride, sodium sulfate, magnesium sulfate, sodium thiosulfate, sodium sulfite, ammonium chloride, ammonium sulfate, and ammonium carbonate;

examples of sugars include simple sugars such as sucrose, fructose, and glucose, and complex sugars such as oligosaccharides and rare sugars; and examples of alcohols include monoalcohols such as methanol, ethanol, 1-propanol and 2-propanol; and glycols such as ethylene glycol and propylene glycol. From the viewpoint of safety, ethanol and 2-propanol are preferable.

Examples of polymers include homopolymers and copolymers of monomers such as ethylene oxide and propylene oxide.

The concentration of the draw substance in the draw solution d is set so that the osmotic pressure of the draw solution d is higher than the osmotic pressure of the raw material liquid a. The osmotic pressure of the draw solution d may fluctuate within that range as long as it is higher than the osmotic pressure of the raw material liquid a.

The method for determining the osmotic pressure difference between the two liquids can be, for example, either of the following methods.

(1) When the two liquids are mixed and then separated into two phases: after the two phases are separated, it is judged that the osmotic pressure of the liquid with the larger volume is higher, or (2) when the two liquids are mixed and not separated into two phases: the two liquids are brought into contact with each other via the forward osmosis membrane o, and it is judged that the osmotic pressure of the liquid the volume of which has increased after a fixed time is high. The fixed time at this time depends on the osmotic pressure difference, but is generally in the range of several minutes to several hours.

<Solvent b of Raw Material Liquid a>

The solvent b in the raw material liquid a is a liquid. The solvent b in the raw material liquid a is preferably capable of dissolving or dispersing the components of the raw material liquid a, and can be selected from any inorganic solvent or organic solvent. The solvent b is commonly water. The solvent b of the present embodiment contains water, acetic acid, acetonitrile, methanol, and 2-propanol as primary components. The solvent b of the raw material liquid a is preferably water, acetic acid, acetonitrile, methanol, and/or 2-propanol, or preferably contains water, acetonitrile, methanol, 2-propanol, or a mixture thereof as primary components. "Primary components" as used herein means that the component is contained in the solvent b in a ratio of more than 50% by mass, 60% by mass or more, 80% by mass or more, 95% by mass or more, or 100% by mass.

<Solvent of Draw Solution d>

The solvent that may be contained in the draw solution d is preferably a solvent of the same type as the solvent b that should be separated from the raw material liquid a. For example, when the solvent of the raw material liquid a is water, it is preferable that the solvent of the draw solution d also be water.

<Concentrated Raw Material Liquid c>

The concentrated raw material liquid c to be obtained by concentrating the raw material liquid a with the forward osmosis membrane unit retains the components in the raw material liquid a, and may be obtained by selectively separating at least a part of solvent b. In the raw material liquid concentration system of the present embodiment, the amount or ratio of the solvent b separated from the raw material liquid a can be arbitrarily controlled.

According to the forward osmosis membrane unit of the embodiment, as long as the osmotic pressure of the raw material liquid a does not exceed the osmotic pressure of the draw solution d, it is possible to concentrate to near the saturation concentration of the raw material liquid a. As a result, even when the amount of the raw material liquid a is large, the time for subsequent treatments (for example, column purification and lyophilization) can be shortened. The time required for lyophilization and column purification increases significantly as the amount of raw material liquid increases. Thus, it is preferable to concentrate the raw material liquid in a preliminary step of freeze-drying and column purification from the viewpoint of shortening treatment time and reducing the energy cost of a pump, heat source, cooling unit, etc.

By carrying out concentration in the forward osmosis membrane unit in this manner until the osmotic pressure of the raw material liquid a becomes sufficiently high, the column purification and freeze-drying can be made more efficient, and the time and energy load of column purification and freeze-drying can be reduced.

The concentration by the forward osmosis membrane unit and the freeze-drying and column purification may be continuously carried out without a time interval, or may be carried out at a predetermined time interval. For example, the concentrated raw material liquid obtained by concentration may be temporarily stored, and freeze-dried and column-purified after a predetermined time has elapsed. However, it is more preferable from the viewpoint of time efficiency that concentration be linked with freeze-drying and column purification, and concentration be continuously carried out without any time interval.

According to the forward osmosis membrane unit, it is possible to obtain a high concentration ratio while maintaining a high degree of raw material liquid components. Furthermore, by changing the draw substance, any concentrate magnification can be obtained, and thus, the types of raw material liquids to which the raw material liquid concentration system of the present embodiment can be applied are various, and substantially any liquid can be concentrated thereby. Therefore, according to the present embodiment, even when it is impossible or difficult to adopt the prior art, it is possible to obtain a high-quality concentrate product with high efficiency.

In particular, the present embodiment relates to a raw material liquid concentration system for a pharmaceutical production process. As described above, when the raw material liquid concentration system of the present embodiment is applied to the concentration of a pharmaceutical or a raw material thereof, it is possible to carry out concentration while maintaining pharmaceutical efficacy.

<Forward Osmosis Membrane Unit>

The forward osmosis membrane unit 11 has the forward osmosis membrane o and an interior space divided into two parts, the raw material liquid-side space R and the draw solution-side space D, by the forward osmosis membrane o.

(Forward Osmosis Membrane o)

The forward osmosis membrane o is a membrane having a function which allows the solvent b to permeate but does not allow a solute to permeate or makes its permeation unlikely. The forward osmosis membrane o may have a function of reverse diffusion r of the draw substance s in the draw solution d into concentrated raw material liquid c.

The forward osmosis membrane o may be a membrane which also functions as a reverse osmosis membrane. However, the reverse osmosis process, in which the solvent is removed by pressure, and the forward osmosis process, which utilizes the difference in osmotic pressure between the raw material liquid and the draw solution, have different appropriate membrane structures due to the differences in the driving force used for solvent removal. In a system used for a forward osmosis process, such as the raw material liquid concentration system of the present embodiment, it is preferable to use a membrane having a higher function as a forward osmosis membrane.

Examples of the form of the forward osmosis membrane o include a hollow fiber membrane form, a flat membrane form, and a spiral membrane form. In a preferred embodiment, the forward osmosis membrane is a hollow fiber membrane.

The forward osmosis membrane o is preferably a composite-type membrane having a separation active layer on the support layer (support membrane). The support membrane may be a flat membrane or a hollow fiber membrane.

When a flat membrane is used as the support membrane, the separation active layer may be present on one side or both sides of the support membrane.

When the hollow fiber membrane is used as a support membrane, the separation active layer may be present on the outer surface or inner surface of the hollow fiber membrane, or on both surfaces.

The support membrane of the present embodiment is a membrane for supporting the separation active layer, and it is preferable that the support membrane itself not substantially exhibit separation performance with respect to the object to be separated. Any membrane including known microporous support membranes and non-woven fabrics can be used as the support membrane.

The preferred support membrane of the present embodiment is a microporous support membrane, and in particular, a microporous hollow fiber support membrane. The fine pore hollow fiber support membrane has fine pores having a pore diameter of preferably 0.001 µm to 0.1 µm, more preferably 0.005 µm to 0.05 µm on the inner surface thereof. Regarding the structure from the inner surface of the microporous hollow fiber support membrane to the outer surface in the depth direction of the membrane, in order to reduce the permeation resistance of the permeating fluid, the structure should preferably be as sparse as possible while maintaining strength. The sparse structure of this portion is preferably, for example, net-like, finger-like voids, or a mixed structure thereof.

As the flat membrane or hollow fiber forward osmosis membrane o, from the viewpoint of the inhibition rate of draw substance, a membrane having a thin film layer containing, as primary components, one or more selected from the group consisting of polyethersulfone, polysulfone, polyketone, polyetheretherketone, polyphenylene ether, polyvinylidene fluoride, polyacrylonitrile, polyimine, polyimide, polybenzoxazole, polybenzimidazole, sulfonated tetrafluoroethylene, and polyamide is preferable.

The polyamide can be formed by interfacial polymerization of polyfunctional acid halides and polyfunctional aromatic amines.

A preferred example of a polyfunctional acid halide is a polyfunctional aromatic acid halide. Polyfunctional aromatic acid halides are aromatic acid halide compounds having two or more acid halide groups in one molecule. Specifically, examples thereof include trimesic acid halides, trimellitic acid halides, isophthalic acid halides, terephthalic acid halides, pyromellitic acid halides, benzophenone tetracarboxylic acid halides, biphenyldicarboxylic acid halides, naphthalenedicarboxylic acid halides, pyridinedicarboxylic acid halides, and benzenedisulfonic acid halides, and these can be used along or a mixture thereof can be used. Examples of the halide ions in these aromatic acid halide compounds include chloride ions, bromide ions, and iodide ions. In this embodiment, in particular, trimesic acid chloride alone, a mixture of trimesic acid chloride and isophthalic acid chloride, or a mixture of trimesic acid chloride and terephthalic acid chloride is preferably used.

Polyfunctional aromatic amines are aromatic amino compounds having two or more amino groups in one molecule. Specifically, examples thereof include m-phenylenediamine, p-phenylenediamine, 3,3'-diaminodiphenylmethane, 4,4'-diaminodiphenylamine, 4,4'-diaminodiphenyl ether, 3,4'-diaminodiphenyl ether, 3,3'-diaminodiphenylamine, 3,5-diaminobenzoic acid, 4,4'-diaminodiphenyl sulfone, 3,3'-diaminodiphenyl sulfone, 3,4'-diaminodiphenyl sulfone, 1,3,5-triaminobenzene, and 1,5-diaminonaphthalene, and these may be used along or a mixture thereof can be used. In the present embodiment, in particular, one or more selected from m-phenylenediamine and p-phenylenediamine are preferably used.

Interfacial polymerization of polyfunctional acid halides and polyfunctional aromatic amines can be carried out according to a conventional method.

"Perfluorosulfonic acid polymer" generally refers to a polymer having a side chain having a sulfonic acid in a main chain skeleton in which a part or all of hydrogen is substituted with fluorine. The perfluorosulfonic acid polymer is used as a chemically stable cation exchange resin or ion selective permeable membrane, for example, in salt electrolysis, polymer electrolyte fuel cells, water electrolysis, or various sensors, and it is commercially available in the form of a membrane or solution under trademarks such as Nafion™ (DuPont), Aciplex™ (Asahi Kasei Chemicals), and Flemion™ (Asahi Glass).

The chemical structure of the perfluorosulfonic acid polymer is not particularly limited, but is typically represented by the following formula (1);
[Chem 1]

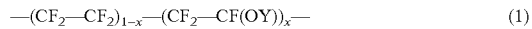  (1)

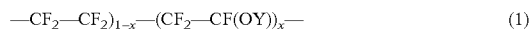  (1)

where Y is $—(CF_2—CF(CF_3)—O—)_m—(CF_2)_n—SO_3H$, x is 0.06 to 0.5, m is an integer of 0 to 2, and n is an integer from 1 to 6. Note that though the sequences of the "$(CF_2—CF_2)$" unit and the "$(CF_2—CF(OY))$" unit are described consecutively for convenience, they may be a block, random, or a combination thereof.

In the present embodiment, it is preferable that a hollow fiber-like forward osmosis membrane be used, and it is particularly preferable that a composite hollow fiber having a separation active layer composed of a polymer thin film on the inner surface of the hollow fiber-like porous support membrane be used.

When a hollow fiber-like forward osmosis membrane is used, the outer diameter of the hollow fiber membrane is, for example, 300 µm to 5,000 µm, preferably 350 µm to 4,000 µm, and the inner diameter of the hollow fiber membrane is, for example, 200 µm to 4,000 µm, preferably 500 µm to 1,500 µm. Though the reason is not clear, if the inner diameter of this hollow fiber membrane is 200 µm or more, the pressure in the hollow fiber during the circulation operation becomes relatively small, and the contact area of the raw material component becomes small. Thus, it is easy to prevent the solute contained in the raw material liquid from adhering to the membrane surface. Such an effect is more easily obtained when the inner diameter of the hollow fiber membrane is 500 µm or more. Conversely, when the inner diameter of the hollow fiber membrane is 4000 µm or less, particularly 1500 µm or less, the contact area of the raw material component is appropriately large, whereby separation efficiency of solvent b is not easily impaired.

In the present embodiment, a plurality of the hollow fiber membranes may form a hollow-fiber fiber bundle. In one aspect, in a raw material liquid concentration system, a plurality of the hollow fiber membrane fiber bundles may preferably be housed in a suitable housing to form a membrane module. In a preferred embodiment, the hollow fiber membranes constituting the hollow-fiber fiber bundle each have a microporous support membrane and a separation active layer which is a polymer thin film provided on the inner surface of the microporous support membrane.

The membrane area of the hollow-fiber fiber bundle is preferably 0.01 m² or more, and more preferably 1 m² or more. The membrane area of the hollow-fiber fiber bundle may be, for example, 20 m² or less, or 10 m² or less from the viewpoint of ease of production of the membrane module.

The permeation flux of the forward osmosis membrane o with respect to the solvent b is preferably 0.1 L/(m²×hr) to 50 L/(m²×hr) as an initial (i.e., at the start of operations) permeation flux of the forward osmosis membrane. Though the reason is not clear, if the initial permeation flux is 0.1 L/(m²×hr) or more, the separation efficiency of the solvent b is not easily impaired, and if it is 50 L/(m²×hr) or less, it is easy to prevent the solute contained in the raw material liquid from adhering to the membrane surface.

The permeation flux with respect to the solvent b in the present disclosure means the amount of solvent b which passes through the forward osmosis membrane o, which is allocated per unit area and per unit time of the forward osmosis membrane o, and is defined by the following formula (1)

$$F = L/(M \times H) \qquad (1)$$

F is the permeation flux (L/(m²×hr)) with respect to the solvent b, L is the amount (L) of solvent b that has passed through, M is the surface area (m²) of the forward osmosis membrane o, and H is the time (hr).

Permeation flux when the solvent b is water is commonly referred to as "permeability." The permeation flux of the solute contained in the draw solution of the present disclosure means the amount of solute in the draw solution passing through the forward osmosis membrane o, which is allocated per unit area and per unit time of the forward osmosis membrane o, and is defined by the following formula (2).

$$F' = L'/(M \times H) \qquad (2)$$

F' is the permeation flux (g/(m²×hr)) with respect to the solute in the draw solution, L' is the amount (g) of solute which has passed, M is the surface area (m²) of the forward osmosis membrane, and H is the time (hr).

In the present disclosure, the ratio (permeation flux of draw substance/permeation flux of solvent) between the permeation flux by which the solute in the draw solution moves into the raw material liquid and the permeation flux of the solvent which moves from the raw material liquid into the draw solution is defined by the following formula (3).

$$R = F'/F \qquad (3)$$

R is the ratio [g/L] of the permeation flux by which the solute in the draw solution moves into the raw material liquid and the permeation flux of the solvent which moves into the draw solution from the raw material liquid.

In one aspect, the ratio (permeation flux of draw substance/permeation flux of the solvent) of the permeation flux by which the solute in the draw solution moves into the raw material liquid to the permeation flux of the solvent b which moves from the raw material liquid to the draw solution is 3 g/L or less. When this ratio is 3 g/L or less, the amount of solute in the draw solution to be moved into the raw material liquid is relatively small, whereby the purity of the raw material liquid can be secured. Furthermore, when the ratio is 0.001 g/L or more, the yield of the raw material liquid is high, which is preferable. Though the reason is not clear, it is presumed that the affinity between the solute contained in the raw material liquid and the forward osmosis membrane is inhibited, whereby the solute is prevented from adhering to the surface of the forward osmosis membrane.

In one aspect, in a scanning electron microscope image obtained by photographing a cross section of the thickness direction of the separation active layer, the coefficient of variation of the thickness of the separation active layer in the radial direction and the longitudinal direction of the hollow-fiber fiber bundle is 0 to 60%. In a preferred embodiment, the membrane area of the hollow-fiber fiber bundle is within the range exemplified above, and the coefficient of variation of the thickness of the separation active layer of the hollow-fiber fiber bundle is within the above range. The coefficient of variation is a value obtained by dividing the standard deviation of the thickness value of the separation active layer at each measurement point by the average value, and is expressed as a percentage (%). There are a total of nine measurement points which are acquired at three positions including the outer peripheral portion, the intermediate portion, and the central portion of the radial direction of the module at both ends and the central portion of the module. For each of the nine locations, the thickness is measured with an n number of 1 or more (the n number at each location is the same).

The thickness at each measurement point is expressed as an average thickness in a measurement range having a length of about 5 to 100 μm. The length of this measuring range is preferably 5 to 50 μm, more preferably 5 to 20 μm, and most preferably 13 μm. As will be described later, the separation active layer of the present embodiment preferably has a fine concave/convex shape on the surface thereof. Thus, when evaluating the thickness of the separation active layer, it is appropriate to evaluate by the average thickness of the measurement range at each measurement point. The separation active layer of the present embodiment has small variations when the average thickness measured at a plurality of measurement points is compared. The direction of the length of the measurement range in the evaluation of the average thickness may be the longitudinal direction of the hollow fibers, the circumferential direction of the hollow fibers, or an oblique direction with respect to the longitudinal direction of the hollow fibers. The directions of the lengths of the measurement ranges in the plurality of scanning electron microscope images used for calculating the average value may be the same direction or different directions from each other.

Each of the coefficient of variation of the average thickness of the separation active layer from the outermost circumference to the center of the hollow-fiber fiber bundle of the present embodiment and the coefficient of variation of the average thickness of the separation active layer from one end of the hollow-fiber fiber bundle to the other end is preferably 0 to 60%, more preferably 0 to 50%, further preferably 0 to 40%, and most preferably 0 to 30%.

The present inventors infer the mechanism by which the surface of the separation active layer of the present embodiment has such a fine concave shape as follows. However, the present invention is not bound by the following theory.

The separation active layer of the present embodiment is preferably formed by interfacial polymerization. In the interfacial polymerization, it is considered that when the liquid film of the first monomer solution formed on the surface of the hollow fibers comes into contact with the second monomer solution, the two do not dissolve in each other and polymerization proceeds at the interface to form a polymerized layer. As a result, it is considered that the formed separation active layer has a shape with many fine concavities and protrusions on the surface thereof. If the separation active layer is formed by a method other than interfacial polymerization, a separation active layer having a shape with many fine surface concavities and protrusions is not formed.

The raw material liquid concentration system according to one aspect is configured so that a pressure of 10 kPa or more and 200 kPa or less is applied from the interior of the hollow fiber membrane, as the forward osmosis membrane, to the exterior thereof. According to such a configuration, the raw material liquid can be concentrated with high efficiency.

The above pressure can be realized by injecting at a predetermined flow rate at a set pressure, for example, by installing a back pressure valve on the discharge pipe of the pump. As the back pressure valve, for example, TESCOM (44-2362-24-595) can be used. The pressure can be measured with a pressure measurement device, for example, manufactured by KEYENCE (GP-M010).

<Flow Paths>

The raw material liquid concentration system 100 according to one aspect has a raw material liquid flow path, a draw solution flow path, a concentrate flow path, and a diluted draw solution flow path. The raw material liquid a, which is the concentration target, is introduced into the raw material liquid-side space R of the forward osmosis membrane unit 11 from the raw material liquid flow path, and the draw solution d is introduced into the draw solution-side space D from the draw solution flow path. The directions of these flows may be countercurrent or parallel to each other. From the forward osmosis membrane unit, the concentrated raw material liquid may be extracted via the concentrate flow path, and the diluted draw solution may be extracted via the diluted draw solution flow path. The diluted draw solution may be regenerated by the draw solution regeneration unit described below.

The linear velocity of the raw material liquid a introduced into the raw material liquid-side space R of the forward osmosis membrane unit is preferably 0.03 cm/s to 15 cm/s. Though the reason is not clear, if the linear velocity is 0.03 cm/s or more, the time for the raw material liquid to contact the membrane does not become excessively long, whereby the solute contained in the raw material liquid is less likely to adhere to the film surface. If it is 15 cm/s or less, the pressure exerted on the membrane does not become excessively large, whereby the solute contained in the raw material liquid is unlikely to adhere to the membrane surface.

The temperature of the raw material liquid a introduced into the raw material liquid-side space R of the forward osmosis membrane unit is preferably 3° C. to 60° C., and more preferably 5° C. to 50° C. Though the reason is not clear, when the temperature of the raw material liquid a is 3° C. or higher, the permeation flux is unlikely to be reduced, and when the temperature is 60° C. or lower, the components in the raw material liquid a are unlikely to be denatured.

The temperature of the draw solution d introduced into the draw solution-side space D of the forward osmosis membrane unit is preferably 5° C. to 60° C., and more preferably 10° C. to 50° C. Though the reason is not clear, when the temperature of draw solution d is 5° C. to 60° C., the amount of draw substance which moves from draw solution d to raw material liquid a via the forward osmosis membrane o is unlikely to increase, which is preferable.

<Temperature Adjustment Mechanism>

The raw material liquid concentration system may comprise a raw material liquid temperature adjustment mechanism and/or a draw solution temperature adjustment mechanism. According to these temperature adjustment mechanisms, the temperature of the raw material liquid and/or the draw solution can be easily controlled within, for example, the above ranges. As the temperature adjustment mechanisms, exhaust heat from a heat exchanger or an industrial process can be used. Utilizing exhaust heat as a heat source is preferable because it can reduce the amount of energy newly consumed for separating the solvent b.

<Draw Solution Regeneration Unit>

The raw material liquid concentration system of the present embodiment may further comprise a draw solution regeneration unit. The draw solution regeneration unit may be, for example, as follows:

(1) a unit (for example, the first draw solution regeneration unit 31 shown in FIG. 3) in which the solvent b is removed from the diluted draw solution e to obtain a regenerated draw solution f, which is a concentrate of the diluted draw solution e, and which supplies the obtained regenerated draw solution f as the draw solution d; and/or (2) a unit (for example, the second draw solution regeneration unit 41 shown in FIG. 4) in which the solvent b is removed from the draw solution d to obtain a concentrated draw solution g, which is a concentrate of the draw solution d, the obtained concentrated draw solution g and the diluted draw solution e are mixed to obtain a mixture (regenerated draw solution f), and the obtained regenerated draw solution f is supplied as the draw solution d.

The first and second draw solution regeneration units may each be, for example, an evaporator. The evaporator may comprise, for example, a distillation device, a forward osmosis membrane, and a membrane distillation unit.

The distillation device may be configured such that after adjusting the diluted draw solution e or draw solution d to a predetermined temperature, it is fed into a distillation column to obtain solvent b from the top of the column, and at the same time, from the bottom of the tower, the regenerated draw solution f, which is a diluted draw solution in which solvent b is removed and concentrated, or concentrated draw solution g, which is a draw solution in which solvent b is removed and concentrated, is obtained.

The forward osmosis membrane may be configured so that the diluted draw solution e or draw solution d is distributed so as to contact the forward osmosis membrane and the solvent b contained in the diluted draw solution e or draw solution d passes through the forward osmosis membrane and is removed, and by this separation, the solvent b and the regenerated draw solution f or the concentrated draw solution g can be generated.

The membrane distillation unit may be a membrane unit having a separation chamber divided into a liquid phase portion and a gas phase portion by a semipermeable membrane. By introducing the diluted draw solution e or the draw solution d into the liquid phase portion of such a membrane unit and reducing the pressure in the gas phase portion, the solvent b contained in the diluted draw solution e or draw solution d moves from the liquid phase portion through the semipermeable membrane to the gas portion part under reduced pressure. As a result, the solvent b can be removed from the diluted draw solution e or the draw solution d to obtain the regenerated draw solution f or the concentrated draw solution g.

As the regeneration unit of the diluted draw solution, a forward osmosis membrane or a membrane distillation unit using a semipermeable membrane is preferable because the equipment size is small, and a membrane distillation unit using a semipermeable membrane is more preferable because the move of the draw substance from diluted draw solution e or draw solution d to solvent b can be suppressed thereby.

The elements used in the membrane distillation unit will be described below.

(Semipermeable Membrane of Membrane Distillation Unit)

Examples of the form of the semipermeable membrane used in the membrane distillation unit include a hollow fiber membrane form, a flat membrane form, and a spiral membrane form.

The flat membrane semipermeable membrane may be composed of, for example, a single layer, or may have a support layer and a separation active layer on the support layer. The hollow fiber semipermeable membrane may be, for example, hollow fibers composed of a single layer, or may have a hollow-fiber support layer and a separation active layer on the outer surface, the inner surface, or both surfaces of the support layer.

The materials of the support layer and the separation active layer in the semipermeable membrane may be any material selected from the materials exemplified above for the forward osmosis membrane o.

The permeation flux of the semipermeable membrane with respect to the solvent b is preferably 1 $L/(m^2 \times hr)$ to 200 $L/(m^2 \times hr)$. When this permeation flux is 1 $L/(m^2 \times hr)$ or more, efficient separation of solvent b is not easily impaired, and when it is 200 $L/(m^2 \times hr)$ or less, the amount of draw substance that moves from draw solution d through the semipermeable membrane to solvent b is unlikely to increase.

This permeation flux is defined in the same manner as the permeation flux of the forward osmosis membrane o with respect to the solvent b.

(Temperature of Diluted Draw Solution e or Draw Solution d to be Introduced into Membrane Distillation Unit)

The temperature of the diluted draw solution e or draw solution d is preferably adjusted to the range of 20° C. to 90° C. prior to introduction into the liquid phase portion of the membrane distillation unit. When this temperature is 20° C. or higher, efficiency of separation of the solvent b by membrane distillation is not easily impaired, and when it is 90° C. or lower, the amount of the draw substance contained in the diluted draw solution e or the draw solution flow d which passes through the semipermeable membrane and moves to the solvent b is unlikely to increase.

As the heat source for heating the diluted draw solution e or the draw solution d, for example, exhaust heat from a heat exchanger or an industrial process can be used. Utilizing exhaust heat as a heat source is preferable because it can reduce the amount of energy newly consumed for separating the solvent b.

(Gas Phase Portion of Membrane Distillation Unit)

The gas phase portion of the membrane distillation unit is preferably depressurized to a predetermined pressure. The pressure of the gas phase part may be appropriately set in accordance with the scale of the device, the concentration of the draw solution d, and the generation rate of the desired solvent b, and for example, it is preferably 0.1 kPa to 80 kPa, and more preferably 1 kPa to 50 kPa.

Examples of the depressurizing device for depressurizing the gas phase portion of the membrane distillation unit include a diaphragm vacuum pump, a dry pump, an oil rotary vacuum pump, an ejector, and an aspirator.

(Product to be Obtained with Draw Solution Regeneration Unit)

According to the first draw solution regeneration unit 31, the solvent b is separated from the diluted draw solution e to produce the regenerated draw solution f, which is a concentrate of a diluted draw solution, and discharged from the membrane distillation unit. The obtained regenerated draw solution f can be reused as the draw solution d after being mixed with the diluted draw solution e and adjusted to a predetermined concentration as needed. When reusing the regenerated draw solution f, the temperature of the regenerated draw solution f may be adjusted using a cooling device.

According to the second draw solution regeneration unit 41, the solvent b is separated from the draw solution d to produce the concentrated draw solution g, which is discharged from the membrane distillation unit. The obtained concentrated draw solution g is mixed with the diluted draw solution e and adjusted to a predetermined concentration to produce the regenerated draw solution f. The regenerated draw solution f can be reused as it is as the draw solution d, or a mixture in which the regenerated draw solution f is mixed with the draw solution can be reused as the draw solution d. When reusing the concentrated draw solution g, the temperature of the concentrated draw solution g may be adjusted using a cooling device.

As the cooling device, for example, a chiller or a heat exchanger can be used.

The solvent b separated from the draw solution d by these draw solution regeneration units may be reused as needed.

<Solute Recovery Rate>

According to the raw material liquid concentration system of the present embodiment as described above, it is possible to obtain a high-concentration concentrate with high efficiency while maintaining the composition of the components (specifically, the solute) contained in the raw material liquid. The higher the degree of maintenance of the component composition by concentration, the higher the recovery rate of the raw material liquid obtained after concentration.

The analysis of the component composition in the obtained concentrate may be appropriately selected in accordance with the type of the raw material liquid and the components contained in the concentrate. Various known analytical methods such as the gravimetric method, ICP-MS (inductively-coupled high-frequency plasma mass spectrometry), the nuclear magnetic resonance spectroscopy (NMR) method, the gas chromatography-mass spectrometry (GC/MS) method, the colorimetric method, the fluorescence method, and high-performance liquid chromatography (HPLC) can be used.

The recovery rate (i.e., the mass of the solute in the concentrate obtained from the raw material liquid with respect to the mass of the solute in the raw material liquid) of the solute by the forward osmosis membrane unit is preferably 70% to 99.9%. More preferably, it is 90% to 99.9%, and further preferably 95% to 99.9%. Since the raw materials are expensive, if the recovery rate is 70% or more, increases in cost can be suppressed. Furthermore, it is practically difficult to obtain a recovery rate exceeding 99.9%.

«Raw Material Liquid Concentration Method»

An aspect of the present invention provides:
a raw material liquid concentration method for a pharmaceutical production process, the method having a first step wherein a raw material liquid containing a solvent and a solute and a draw solution containing a draw substance are contacted via a forward osmosis membrane to move the solvent in the raw material liquid into the draw solution and move the draw substance in the draw solution into the raw material liquid to obtain a concentrated raw material liquid and a diluted draw solution.

In the aspect, the method may be executed using the raw material liquid concentration system described above. Thus, the components such as the forward osmosis membrane (hollow fiber membrane, etc.), the membrane module, the raw material liquid, and the draw solution used in the method may be the same as those exemplified in the section «Raw Material Liquid Concentration System».

Suitable examples of each step of the raw material liquid concentration method will be described below.

In the first step, one or two or more of:
supplying raw material liquid and draw solution from the interior of the hollow fiber as the forward osmosis membrane to the exterior so that a pressure of 10 kPa to 200 kPa is applied,
the temperature of the raw material liquid is adjusted to the range of 5° C. to 50° C.,
the circulation linear velocity at which the concentrated raw material liquid circulates is set to 0.03 cm/s to 15 cm/s, and
the initial permeation flux of the forward osmosis membrane is set to 0.1 L/(m$^2$×hr) to 50 L/(m$^2$×hr), as exemplified in the section «Raw Material Liquid Concentration System», may be carried out.

The raw material liquid concentration method may further comprise a first draw solution regeneration step in which the solvent is removed from the diluted draw solution to obtain a regenerated draw solution, and the regenerated draw solution is used again as the draw solution. The first draw solution regeneration step may be executed using the first draw solution regeneration unit exemplified in the section «Raw Material Liquid Concentration System».

In one aspect, the removal of the solvent from the diluted draw solution in the first draw solution regeneration step is carried out by evaporation means. The evaporation means may be an evaporator as exemplified in the section «Raw Material Liquid Concentration System».

The raw material liquid concentration method may further have a second draw solution regeneration step in which the solvent is removed from the draw solution to obtain a concentrated draw solution, and a mixture of the concentrated draw solution and the diluted draw solution is used as the draw solution. The second draw solution regeneration step may be executed using the second draw solution regeneration unit exemplified in the section «Raw Material Liquid Concentration System».

In one aspect, the removal of the solvent from the draw solution in the second draw solution regeneration step is carried out by evaporation means. The evaporation means may be an evaporator as exemplified in the section «Raw Material Liquid Concentration System».

EXAMPLES

The present invention will be specifically described below based on the Examples, but the present invention is not limited by the Examples below. Each physical property is measured by the following method.

(1) Draw Solution Permeation Flux (g/m$^2$/hr)

The permeation flux of the draw substance, by which the draw substance in the draw solution moves into the raw material liquid, is measured by the following method. After operation is complete, the amount of solute contained in the draw solution contained in the concentrated raw material liquid is measured using an ICP-MS manufactured by Thermo Fisher Scientific Co., Ltd., type "iCAP Q." The permeation flux of the solution moved by driving is calculated from the formula (3) above.

(2) Circulation Linear Velocity (cm/s)

The linear velocity of concentrated raw material liquid in the circulation mechanism was calculated by the following formula.

$$X = Y/Z$$

where X is the linear velocity of the concentrated raw material liquid [cm/s], Y is the flow velocity of the concentrated raw material liquid [cm³/s], and Z is the total hollow fiber inner cross-sectional area [cm²]. The flow velocity of the concentrated raw material liquid is measured using an "FD-X" manufactured by Keyence Corporation.

Example 1

The following Examples were carried out using the raw material liquid concentration system 500 having the structure shown in FIG. 5.

«Raw Material Liquid Concentration System Production»
<Production of Forward Osmosis Membrane Unit 11 Having Forward Osmosis Membrane o>
(1) Production of Hollow Fiber Support Membrane Module A 20% by mass hollow fiber spinning stock solution was prepared by dissolving polyether sulfone (PES: manufactured by BASF, product name "Ultrason") in N-methyl-2-pyrrolidone (manufactured by Wako Pure Chemical Industries, Ltd.). A wet hollow fiber spinning machine equipped with a double spinner was filled with the above stock solution and extruded into a coagulation tank filled with water to form hollow fibers by phase separation. The obtained hollow fibers were wound on a winder. The outer diameters of the obtained hollow fibers were 1.0 mm, the inner diameters were 0.7 mm, and the diameters of the fine pores on the inner surface were 0.05 µm. This hollow fiber was used as a support membrane.

A membrane module having an effective membrane inner surface product of 0.023 m² was prepared by filling 130 of the hollow fiber support membranes in a cylindrical plastic housing having a diameter of 2 cm and a length of 10 cm, and affixing both ends thereof with an adhesive.

(2) Forward Osmosis Membrane Unit Production 10 g of m-phenylenediamine and 0.8 g of sodium lauryl sulfate were charged into a 0.5 L container, and 489.2 g of pure water was further added thereto for dissolution to prepare 0.5 kg of a first solution used for interfacial polymerization.

0.8 g of trimesic acid chloride was charged into another 0.5 L container, and 399.2 g of n-hexane was added thereto for dissolution to prepare 0.4 kg of a second solution used for interfacial polymerization.

The core side of the membrane module (inside the hollow fibers) was filled with the first solution, allowed to stand for 30 minutes, and then the liquid was drained to form a thin liquid film of the first solution inside the hollow fiber.

Next, a core-side pressure adjusting device was used to set the core-side pressure to normal pressure, and a shell-side pressure adjusting device was used to set the shell-side pressure to a depressurization of 10 kPa as an absolute pressure. After standing for 30 minutes in this state, while maintaining these pressures, the second solution was pumped to the core side by a second solution feed pump at a flow rate of 1.5 L/min for 3 minutes to carry out interfacial polymerization. The polymerization temperature was 25° C.

Next, the membrane module was removed from the device, and nitrogen at 50° C. was flowed to the core side for 30 minutes to purge the n-hexane.

Next, hot water at 85° C. was flowed inside the hollow fiber for 30 minutes, then the module was placed in an autoclave (ES-315 manufactured by Tomy Seiko Co., Ltd.), and high-temperature steam at 121° C. was applied for 20 minutes. By washing with water at 20° C. for 30 minutes or more, a forward osmosis membrane unit 11, which is a module of a hollow fiber forward osmosis membrane o having a separation active layer composed of polyamide on the inner surface of the hollow fiber support membrane, was prepared.

<Diluted Draw Solution Concentration>
(Membrane Distillation Unit Production)

23 parts by mass of hydrophobic silica (manufactured by Nippon Aerosil Co., Ltd., product name "AEROSIL-R972") having an average primary particle size of 0.016 µm and a specific surface area of 110 m²/g, 31 parts by mass of dioctyl phthalate (DOP), and 6 parts by mass of dibutyl phthalate (DBP) were mixed with a Henschel mixer, and thereafter, 40 parts by mass of polyvinylidene fluoride (manufactured by SOLVAY, product name "Solef6010") having a weight average molecular weight of 310,000 was added thereto and mixed again with a Henschel mixer to obtain a mixture. This mixture was pelletized with a twin-screw kneading extruder.

The obtained pellets were melt-kneaded at 240° C. with a twin-screw kneading extruder and extruded into hollow fiber shapes to obtain hollow fibers. At this time, by attaching a hollow fiber formation spout to the extrusion port in the head at the tip of the extruder, extruding the kneaded melt from the melt extrusion circular hole, and simultaneously discharging nitrogen gas from the circular hole for hollow portion formation fluid discharge inside the melt extrusion circular hole, extrusion into a hollow fiber form was carried out.

The hollow fibers were introduced into a water bath (40° C.) at a free running distance of 20 cm and wound at a speed of 20 m/min.

The obtained hollow fibers were continuously drawn by a pair of first endless track-type belt pickers at a speed of 20 m/min, were passed through a first heating tank (0.8 m length) controlled to a spatial temperature of 40° C., and thereafter, were drawn at a speed of 40 m/min by a second endless track-type belt picker and stretched to 2.0 times magnification in the longitudinal direction. Next, after passing through a second heating tank (0.8 m length) controlled to a spatial temperature of 80° C., the fibers were cooled while being periodically bent on the water surface of a cooling water tank at 20° C., and thereafter, were drawn at a speed of 30 m/min by a third endless track-type belt picker, and the drawn fibers were contracted (relaxed) up to 1.5 times magnification in the longitudinal direction, and then wound with a skein with a circumference of about 3 m. Periodic bending on the water surface of the cooling water tank was carried out by continuously sandwiching the hollow fibers at a rotation speed of 170 rpm using a pair of concave-convex rollers having a peripheral length of about 0.20 m and four protrusions.

The hollow fibers after the above treatment were immersed in methylene chloride to extract and remove the DOP and DBP, and then dried. Next, the hollow fibers were immersed in a 50 mass % ethyl alcohol aqueous solution and then immersed in a 5 mass % sodium hydroxide aqueous solution at 40° C. for 1 hour to extract and remove the silica. They were then washed with water and dried to obtain a hollow fiber membrane. The outer diameter of the obtained hollow fiber was 1.25 mm, the inner diameter was 0.70 mm, and the diameter of the fine pores on the inner surface was 0.1 μm. These hollow fibers were used as a porous membrane.

A membrane distillation unit, which is a module of a hollow fiber porous membrane having an effective membrane inner surface area of 0.012 m², was prepared by filling 70 porous membranes composed of the above hollow fibers into a cylindrical plastic housing having a diameter of 2 cm and a length of 10 cm, and affixing both ends with an adhesive.

The permeation flux (permeability) of water in this membrane distillation unit measured using pure water as the treatment solution and 3.5 mass % saline as the draw solution was 20.02 L/(m²×hr).

In Example 1, concentration of an L-alanyl-L-glutamine aqueous solution was carried out. The circulation mechanism 21 was used as needed.

(1) First Step

An aqueous solution of L-alanyl-L-glutamine as the raw material liquid a was prepared as follows.

10 g of commercially available L-alanyl-L-glutamine (white powder state, manufactured by Nacalai Tesque, Inc.) was dissolved in a solution of ion-exchanged water/acetonitrile=85/15 (volume ratio) at 25° C. to obtain 1 L of a 10 g/L L-alanyl-L-glutamine aqueous solution.

In Example 1, concentration of the L-alanyl-L-glutamine aqueous solution described above was carried out using the raw material liquid concentration system 500 having the configuration shown in FIG. 5.

The raw material liquid a (L-alanyl-L-glutamine aqueous solution) was flowed through the forward osmosis membrane unit 11 of the raw material liquid concentration system 500 shown in FIG. 5 at a linear speed of 3.3 cm/s, and the draw solution d was flowed at a linear speed of 1.9 cm/s. At this time, the temperature of the raw material liquid a was maintained at 25° C., and filtration was carried out by the cross-flow method.

An aqueous solution containing 20% by mass of magnesium chloride as the draw substance was used as the draw solution d. 1 L of the raw material liquid a was concentrated to 100 cm³ while being circulated using the circulation mechanism 21 as necessary. The circulation mechanism was not used when concentration to the predetermined concentration could be carried out after passing through the forward osmosis membrane unit once.

(2) Draw Solution Regeneration Step

The draw solution regeneration step was carried out using the membrane distillation unit produced above in order to maintain a constant concentration of the draw substance of the draw solution. The draw solution d was flowed through the membrane distillation unit described above at a flow velocity of 600 ml/min, and the pressure of the gas phase portion of the membrane distillation unit was adjusted with a vacuum pump so that the absolute pressure was 10 kPa, and membrane distillation was carried out to obtain the concentrated draw solution g.

The diluted draw solution e obtained in the first step and the concentrated draw solution g obtained by membrane distillation were mixed in a buffer tank to prepare (regenerate) draw solution d, which was circularly used in the first step.

(Measurement of Initial Permeation Flux of Solvent Moved from Raw Material Liquid a into Draw Solution)

One minute after the start of the operation, the amount (L) of the solvent b permeated from the raw material liquid a into the draw solution, which moved during the operation, was measured with an electronic balance (GX-12K) manufactured by A & D Company, Ltd. The initial permeation flux of the solvent moved by the operation was calculated from the above formula (1). The calculation results are shown in Table 1.

(Measurement of Permeation Flux of Solvent Moved from Raw Material Liquid a into Draw Solution)

Immediately after the end of the operation, the amount (L) of the solvent b permeated from the raw material liquid a into the draw solution, which was moved during the operation, was measured with an electronic balance (GX-12K) manufactured by A & D Company, Ltd. The permeation flux of the solvent moved by driving was calculated from the above formula (1).

(Measurement of Permeation Flux of Solute Contained in Draw Solution Moved into Raw Material Liquid a)

After the operation was completed, the amount of solute contained in the draw solution contained in the concentrated raw material liquid was measured using an ICP-MS manufactured by Thermo Fisher Scientific, Inc., type "iCAP Q." The permeation flux of the solution moved by driving was calculated from the above formula (2).

Using the above calculation result, the ratio of the permeation flux of the solute permeated from the draw solution into the raw material liquid to the permeation flux of the solvent permeated into the draw solution from the raw material liquid was calculated from the above formula (3). The calculation results are shown in Table 1.

(Recovery Rate of Solute of Raw Material Liquid)

Each sample was dissolved in a deuterium and analyzed by $^1$H-NMR for the aqueous solution before concentration and the dilute solution obtained by dissolving the obtained concentrate with a solvent so that the amount of the solution was 1 L. For data processing, phase correction and baseline correction were carried out, and the chemical shift was corrected so that the signal of the methyl group of 3-(trimethylsilyl)-1-propane-1,1,2,2,3,3-d6-sodium sulfonate (DSS-d6) was 0 ppm. The $^1$H-NMR measurement conditions were as follows.

Measurement device: "ECS-400" (400 MHz) manufactured by JEOL Ltd.

Sample amount: 10 μm

Deuterium: Deuterium oxide (manufactured by Tokyo Chemical Industry Co., Ltd.): 700 μm Interior standard substance: DSS-d6 (manufactured by Fuji Film Wako Pure Chemical Industries, Ltd.); 0.007 mol/L In the obtained $^1$H-NMR spectrum, the peak area values between 0.2 and 4 ppm and between 6 and 10 ppm were obtained when the peak area of the methyl group of 0 ppm DSS-d6 was set to 100, and the recovery rate of raw material liquid a after concentrate was calculated from the peak area value after concentrate/the peak area value before concentrate×100, and evaluated according to the following criteria. When the organic solvent was contained, the area value was calculated excluding the corresponding NMR peak. The results are shown in Table 1.

A: When the recovery rate was 95% or more.

B: When the recovery rate was 90% or more and less than 95%.

C: When the recovery rate was 70% or more and less than 90%.

D: When the recovery rate was less than 70%.

(Purity of Raw Material Liquid)

From the concentration of the aqueous solution before concentration and the volume reduction rate at the concentration, the concentration of the apparent raw material aqueous solution after concentration and the amount of the apparent raw material contained in the raw material liquid when the recovery rate was 100% were calculated. Next, the true amount of raw material contained in the raw material liquid after concentration was calculated from the apparent amount of raw material multiplied by the recovery rate.

Furthermore, the amount of solute contained in the draw solution contained in the concentrated raw material liquid was measured using an ICP-MS manufactured by Thermo Fisher Scientific Co., Ltd., type "iCAP Q."

The purity of the raw material liquid after concentration was calculated from the formula "(true amount of raw material after concentration−amount of solute contained in draw solution contained in concentrated raw material liquid)/true amount of raw material after concentration×100" and evaluated according to the following criteria. The results are shown in Table 1.
  A: When the purity was 90% or more.
  B: When the purity was 70% or more and less than 90%.
  C: When the purity was 50% or more and less than 70%.
(3) Scanning Electron Microscopy Observation of Separation Active Layer, Measurement of Average Thickness and Coefficient of Variation The hollow fiber membrane modules obtained in each of the examples and comparative examples were disassembled, the hollow-fiber fiber bundles were disassembled from three locations: the center of the radial direction, the position of 50% of the radius, and the outermost circumference, and the hollow fibers were sampled one-by-one. Each hollow fiber was divided into three equal parts in the longitudinal direction to obtain nine samples. Each of these hollow fiber samples was frozen and split to prepare a hollow fiber cross-section sample.

The samples were prepared by freezing and splitting as follows.

The hollow fibers were immersed in ethanol (manufactured by Wako Pure Chemical Industries, Ltd.), and after encapsulating in a gelatin capsule No. 00 (manufactured by Wako Pure Chemical Industries, Ltd.) together with ethanol, were immersed in liquefied nitrogen for 5 minutes and frozen. The hollow fibers were cut together with the frozen capsules using a chisel and a mallet. Then, the obtained cut pieces were freeze-dried to obtain a hollow fiber cross-section sample for observation with a scanning electron microscope.

Scanning electron microscope observation was carried out on each of the above cross-section samples. Scanning electron microscope observation was carried out using a model S-4800 manufactured by Hitachi, Ltd., under the conditions of an acceleration voltage of 1.0 kV, a WD of 5 mm reference±0.7 mm, and an emission current setting of 10±1 µA. The microscope image was printed on paper with a printer, the separation active layer part was cut out, and the mass was measured with a precision balance. This mass was converted into the thickness (µm) of the separation active layer by a calibration curve prepared in advance. Then, the coefficient of variation was calculated using the average value of the nine samples as the average thickness of the separation active layer. The results are shown in Table 1.

Example 2

As the draw solution d, an aqueous solution containing 10% by mass of magnesium chloride was used as the draw substance. Other than this, evaluation was carried out under the same conditions as in Example 1. The results are shown in Table 1.

Example 3

Evaluation was carried out under the same conditions as in Example 2 except that a pressure of 100 kPa was applied from the inside to the outside of the hollow fibers. The results are shown in Table 1.

Example 4

Evaluation was carried out under the same conditions as in Example 2 except that water was used as the solvent b. The results are shown in Table 1.

Example 5

Evaluation was carried out under the same conditions as in Example 3 except that water was used as the solvent b. The results are shown in Table 1.

Example 6

Evaluation was carried out under the same conditions as in Example 2 except that a pressure of 10 kPa was applied from the inside to the outside of the hollow fibers. The results are shown in Table 1.

Example 7

Evaluation was carried out under the same conditions as in Example 2 except that a pressure of 200 kPa was applied from the inside to the outside of the hollow fibers. The results are shown in Table 1.

Example 8

Evaluation was carried out under the same conditions as in Example 1 except that interfacial polymerization was carried out as follows.

10 g of m-phenylenediamine and 0.8 g of sodium lauryl sulfate were charged into a 0.5 L container, and 489.2 g of pure water was further added thereto for dissolution to prepare 0.5 kg of the first solution used for interfacial polymerization.

0.8 g of trimesic acid chloride was charged into another 0.5 L container, and 399.2 g of n-hexane was added thereto for dissolution to prepare 0.4 kg of a second solution used for interfacial polymerization.

The core side (inside the hollow fiber) of the microporous hollow fiber membrane module was filled with the first solution, allowed to stand for 30 minutes, and then drained to form a thin liquid film of the first solution inside the hollow fibers.

Next, the core side pressure was set to normal pressure by the core side pressure adjusting device, and the shell side pressure was set to 10 kPa as an absolute pressure by the shell side pressure adjusting device. After standing for 30 minutes in this state, while maintaining this pressure, the second solution was pumped to the core side by the second solution feed pump at a flow rate of 1.5 L/min for 3 minutes to carry out interfacial polymerization. The polymerization temperature was 25° C.

Next, the hollow fiber membrane module was removed from the device, and nitrogen at 50° C. was flowed to the core side for 30 minutes to purge the n-hexane. Further, both the shell side and the core side were washed with pure water to produce a hollow fiber support membrane module.

Next, nitrogen at 50° C. was flowed through the core side of the hollow fiber support membrane module for 30 minutes to evaporate and remove the n-hexane. Next, hot water at 85° C. was poured inside the hollow fiber for 30 minutes, and thereafter, the hollow fiber support membrane module was placed in an autoclave (ES-315 manufactured by Tomy Seiko Co., Ltd.), and high-temperature steam at 121° C. was applied for 20 minutes, and washing was carried out with water at 20° C. for 30 minutes or more. Furthermore, 50 KPa was applied from the shell side (outside of the hollow fiber) of the hollow fiber support membrane module. Thereafter, both the shell side and the core side were washed with pure water, whereby a forward osmosis membrane unit 11, which is a module of a hollow fiber-like forward osmosis membrane o having a separation active layer composed of polyamide on the inner surface of the hollow fiber support membrane, was prepared. The results are shown in Table 1.

Example 9

Evaluation was carried out under the same conditions as in Example 1 except that interfacial polymerization was carried out as follows.

10 g of m-phenylenediamine and 0.8 g of sodium lauryl sulfate were charged into a 0.5 L container, and 489.2 g of pure water was further added thereto for dissolution to prepare 0.5 kg of the first solution used for interfacial polymerization.

0.8 g of trimesic acid chloride was charged into another 0.5 L container, and 399.2 g of n-hexane was added thereto for dissolution to prepare 0.4 kg of a second solution used for interfacial polymerization.

The core side (inside the hollow fibers) of the microporous hollow fiber membrane module was filled with the first solution, allowed to stand for 30 minutes, and then drained to form a thin liquid film of the first solution inside the hollow fiber.

Next, the core side pressure was set to normal pressure by the core side pressure adjusting device, and the shell side pressure was set to 10 kPa as an absolute pressure by the shell side pressure adjusting device. After allowing to stand for 30 minutes in this state, while maintaining this pressure, the second solution was pumped to the core side by the second solution feed pump at a flow rate of 1.5 L/min for 3 minutes to carry out interfacial polymerization. The polymerization temperature was 25° C.

Next, the hollow fiber membrane module was removed from the device, and nitrogen at 50° C. was flowed to the core side for 30 minutes to purge the n-hexane. Both the shell side and the core side were washed with pure water to produce the hollow fiber support membrane module.

Next, nitrogen at 50° C. was flowed through the core side of the hollow fiber support membrane module for 30 minutes to evaporate and remove the n-hexane. Next, hot water at 85° C. was poured inside the hollow fiber for 30 minutes, and then the hollow fiber support membrane module was placed in an autoclave (ES-315 manufactured by Tomy Seiko Co., Ltd.), and high-temperature steam at 121° C. was applied thereto for 20 minutes. Further, it was then washed with water at 20° C. for 30 minutes or more. Further, a pressure of 70 KPa was applied from the shell side (outside of the hollow fibers) of the hollow fiber support membrane. Thereafter, both the shell side and the core side are washed with pure water, whereby a forward osmosis membrane unit 11, which is a module of a hollow fiber-like forward osmosis membrane o having a separation active layer composed of polyamide on the inner surface of the hollow fiber support membrane, was prepared. The results are shown in Table 1.

Example 10

Evaluation was carried out under the same conditions as in Example 1 except that the interfacial polymerization was carried out as follows.

10 g of m-phenylenediamine and 0.8 g of sodium lauryl sulfate were charged into a 0.5 L container, and 489.2 g of pure water was further added thereto for dissolution to prepare 0.5 kg of the first solution used for interfacial polymerization.

0.8 g of trimesic acid chloride was charged into another 0.5 L container, and 399.2 g of n-hexane was added thereto for dissolution to prepare 0.4 kg of a second solution used for interfacial polymerization.

The core side (inside the hollow fibers) of the microporous hollow fiber membrane module was filled with the first solution, allowed to stand for 30 minutes, and then drained to form a thin liquid film of the first solution inside the hollow fiber.

Next, the core side pressure was set to normal pressure by the core side pressure adjusting device, and the shell side pressure was set to 10 kPa as an absolute pressure by the shell side pressure adjusting device. After allowing to stand for 30 minutes in this state, while maintaining this pressure, the second solution was pumped to the core side by the second solution feed pump at a flow rate of 1.5 L/min for 3 minutes to carry out interfacial polymerization. The polymerization temperature was 25° C.

Next, the hollow fiber membrane module was removed from the device, and nitrogen at 50° C. was flowed to the core side for 30 minutes to fly n-hexane. Further, a hollow fiber support membrane module was produced by washing both the shell side and the core side with pure water.

Next, nitrogen at 50° C. was flowed through the core side of the hollow fiber support membrane module for 30 minutes to evaporate and remove the n-hexane. Next, hot water at 85° C. was flowed inside the hollow fibers for 30 minutes, and the hollow fiber support membrane module was then placed in an autoclave (ES-315 manufactured by Tomy Seiko Co., Ltd.), and high-temperature steam at 121° C. was applied thereto for 20 minutes. Further, it was washed with water at 20° C. for 30 minutes or more. 100 kPa was applied from the shell side (outside of the hollow fibers) of the hollow fiber support membrane module. Thereafter, both the shell side and the core side were washed with pure water, whereby a forward osmosis membrane unit 11, which is a module of a hollow fiber-like forward osmosis membrane o having a separation active layer composed of polyamide on the inner surface of the hollow fiber support membrane, was prepared. The results are shown in Table 1.

Examples 11 to 16

Evaluation was carried out under the same conditions as in Example 1 except that the linear velocity of the raw material liquid a (L-alanyl-L-glutamine aqueous solution) and the temperature of the raw material liquid a were changed to the conditions shown in Table 1. The results are shown in Table 1.

Example 17

Evaluation was carried out under the same conditions as in Example 2 except that the microporous hollow fiber membrane was composed of polysulfone hollow fibers. The polysulfone hollow fiber membrane module was prepared as follows.

Polysulfone (P-3500 manufactured by Amoco Co., Ltd.) was dissolved in N-methyl-2-pyrrolidone (manufactured by Wako Pure Chemical Industries, Ltd.) so as to achieve a content of 19% by mass to prepare a hollow fiber spinning stock solution. A wet hollow fiber spinning machine equipped with a double spinner was filled with the above stock solution, which was extruded into a coagulation tank filled with water to form hollow fibers by phase separation. The obtained hollow fibers were wound on a winder. The outer diameters of the obtained hollow fibers were 1.0 mm, and the inner diameters were 0.70 mm. These hollow fibers were used as a forward osmosis membrane. 130 of the forward osmosis membranes were filled in a cylindrical plastic housing having a diameter of 2 cm and a length of 10 cm, and both ends thereof were affixed with an adhesive, whereby a forward osmosis membrane unit 11 having an effective membrane inner surface product of 0.023 m² was prepared. The results are shown in Table 1.

Example 18

Evaluation was carried out under the same conditions as in Example 2 except that the hollow fiber membrane was composed of polyketone hollow fibers. The polyketone hollow fiber membrane module was prepared as follows.

A polyketone having an intrinsic viscosity of 3.4 dl/g, in which ethylene and carbon monoxide were completely alternately copolymerized, was added to a 65 mass % resorcin aqueous solution at a polymer concentration of 10.7 mass %, and the mixture was stirred and dissolved at 80° C. for 2 hours to remove the polyketone. A uniform and transparent undiluted solution was obtained by foaming.

A wet hollow fiber spinning machine equipped with a double spinner was filled with the above stock solution at 50° C., which was extruded into a coagulation tank filled with water to form hollow fibers by phase separation. The obtained hollow fibers were wound on a winder. The outer diameters of the obtained hollow fibers were 1.0 mm, the inner diameters were 0.7 mm, and the diameters of the fine pores on the inner surface were 0.15 μm.

These hollow fibers were used as a forward osmosis membrane. 130 of the forward osmosis membranes were filled in a cylindrical plastic housing having a diameter of 2 cm and a length of 10 cm, and both ends thereof were affixed with an adhesive to prepare a forward osmosis membrane unit 11 having an effective membrane inner surface area of 0.023 m². The results are shown in Table 1.

Example 19

Evaluation was carried out under the same conditions as in Example 1 except that the solvent b was set to water/methanol=90/10 in terms of a volume ratio. The results are shown in Table 1.

Example 20

Evaluation was carried out under the same conditions as in Example 1 except that the solvent b was set to water/2-propanol=90/10 in terms of a volume ratio. The results are shown in Table 1.

Example 21

Evaluation was carried out under the same conditions as in Example 1 except that the raw material liquid was an aqueous solution of an oligonucleotide (base number 10) having a molecular weight of 3300. The results are shown in Table 1.
<Raw Material Liquid>

As the raw material liquid, an aqueous solution of an oligonucleotide (base number 10) having a molecular weight of 3300 was used. Water was used as the solvent b.

The aqueous solution of the oligonucleotide (base number 10) having a molecular weight of 3300 as the raw material liquid a was prepared as follows. 10 g of an oligonucleotide (base number 10) having a molecular weight of 3300 was charged into a closed container composed of SUS304 and having a capacity of 3.0 L, and distilled water was added thereto to obtain a 1 L aqueous solution. The obtained aqueous solution was stirred for 30 minutes to obtain a raw material liquid. The results are shown in Table 1.

Example 22

Evaluation was carried out under the same conditions as in Example 1 except that the raw material liquid was an aqueous solution of asparagine.
<Raw Material Liquid>

As the raw material liquid, an aqueous solution of asparagine was used. Water was used as the solvent b.

The aqueous solution of asparagine as the raw material liquid a was prepared as follows. 10 g of asparagine was charged into a closed container composed of SUS304 having a capacity of 3.0 L, and distilled water was added thereto to obtain a 1 L aqueous solution. The obtained aqueous solution was stirred for 30 minutes to obtain a raw material liquid. The results are shown in Table 1.

Example 23

Evaluation was carried out under the same conditions as in Example 1 except that the raw material liquid was an aqueous solution of streptomycin.
<Raw Material Liquid>

An aqueous solution of streptomycin was used as the raw material liquid a. Water was used as the solvent b.

The aqueous solution of streptomycin as the raw material liquid a was prepared as follows. 10 g of streptomycin was charged into a closed container composed of SUS304 having a capacity of 3.0 L, and distilled water was added thereto to obtain a 1 L aqueous solution. The obtained aqueous solution was stirred for 30 minutes to obtain a raw material liquid. The results are shown in Table 1.

Example 24

Evaluation was carried out under the same conditions as in Example 1 except that the raw material liquid was an aqueous solution of mitomycin C.
<Raw Material Liquid>

An aqueous solution of mitomycin C was used as the raw material liquid. Water was used as the solvent b.

The aqueous solution of mitomycin C as the raw material liquid a was prepared as follows. 10 g of mitomycin C was charged into a closed container composed of SUS304 having a capacity of 3.0 L, and distilled water was added thereto to obtain a 1 L aqueous solution. The obtained aqueous solution was stirred for 30 minutes to obtain a raw material liquid. The results are shown in Table 1.

Example 25

Evaluation was carried out under the same conditions as in Example 1 except that an aqueous solution of vitamin A was used as the raw material liquid of Example 1.
<Raw Material Liquid>
An aqueous solution of vitamin A was used as the raw material liquid. Water was used as the solvent b.

The aqueous vitamin A solution as the raw material liquid a was prepared as follows. 10 g of vitamin A was charged into a closed container composed of SUS304 having a capacity of 3.0 L, and distilled water was added thereto to obtain a 1 L aqueous solution. The obtained aqueous solution was stirred for 30 minutes to obtain a raw material liquid. The results are shown in Table 1.

Example 26

As the draw solution d, an aqueous solution containing 25% by mass of a magnesium sulfate aqueous solution as the draw substance was used. Other than this, evaluation was carried out under the same conditions as in Example 1. The results are shown in Table 1.

Example 27

An aqueous solution containing 20% by mass of an aqueous sodium chloride solution as the draw substance as the draw solution d. Other than this, evaluation was carried out under the same conditions as in Example 1. The results are shown in Table 1.

Example 28 (Reference Example)

As the draw solution d, an aqueous solution containing 50% by mass of a sucrose aqueous solution as the draw substance was used. Other than this, evaluation was carried out under the same conditions as in Example 1. The results are shown in Table 1.

Comparative Example 1

Evaluation was carried out using an ultrafiltration device instead of a forward osmosis membrane unit.

Treatment was carried out by a cross-flow filtration method under the conditions of a linear velocity of 100 cm/s, an operating temperature of 25° C., and an intermembrane differential pressure (TMP) of about 0.05 MPa using a Hydrosart™/Sartocon Slice Cassette (exclusion limit molecular weight: 10K, membrane area: 0.1 m$^2$, material: regenerated cellulose membrane, manufactured by Sartorius AG) attached to a membrane holder (Sartcon Slice Holder, manufactured by Sartorius AG) as the ultrafiltration membrane and using a pump (Rikiport NE1.300, manufactured by KNE).
(Measurement of Initial Permeation Flux of Solvent Moved from Raw Material Liquid a)

The amount (L) of solvent b permeated from the raw material liquid a, which moved during operation, was measured with an electronic balance (GX-12K) manufactured by A & D Co., Ltd. The initial permeation flux of the solvent moved by operation was calculated from the above formula (1). The calculation results are shown in Table 2.
(Recovery Rate of Solute of Raw Material Liquid)

Each sample was dissolved in a deuterium and analyzed by $^1$H-NMR for the aqueous solution before concentration and the dilute solution obtained by dissolving the obtained concentrate with a solvent so that the amount of the solution was 1 L. For data processing, phase correction and baseline correction were carried out, and the chemical shift was corrected so that the signal of the methyl group of 3-(trimethylsilyl)-1-propane-1,1,2,2,3,3-d6-sodium sulfonate (DSS-d6) was 0 ppm. The $^1$H-NMR measurement conditions were as follows.

Measurement device: "ECS-400" (400 MHz) manufactured by JEOL Ltd.

Sample amount: 10 μL

Deuterated solvent: Deuterium oxide (manufactured by Tokyo Chemical Industry Co., Ltd.): 700 μL Interior standard substance: DSS-d6 (manufactured by Fuji Film Wako Pure Chemical Industries, Ltd.); 0.007 mol/L In the obtained $^1$H-NMR spectrum, the peak area values between 0.2 and 4 ppm and between 6 and 10 ppm were obtained when the peak area of the methyl group of 0 ppm DSS-d6 was set to 100, and the recovery rate of raw material liquid a after concentrate was calculated from the peak area value after concentrate/the peak area value before concentrate×100, and evaluated according to the following criteria. When the organic solvent was contained, the area value was calculated excluding the corresponding NMR peak. The results are shown in Table 2.

A: When the recovery rate was 95% or more.

B: When the recovery rate was 90% or more and less than 95%.

C: When the recovery rate was 70% or more and less than 90%.

D: When the recovery rate was less than 70%.

Comparative Example 2

Evaluation was carried out under the same conditions as in Comparative Example 1, except that a reverse osmosis membrane was used instead of the ultrafiltration membrane. Product number "NTR-759HR" manufactured by Nitto Denko KK was used as the reverse osmosis membrane, and the raw material liquid a was concentrated at a linear speed of 10 cm/s, an operating temperature of 25° C., and an operating pressure of 3.0 MPa. The results are shown in Table 2.

Comparative Example 3

Evaluation was carried out under the same conditions as in Comparative Example 1 except that a distillation column incorporating a vacuum system was used in place of the ultrafiltration membrane, and vacuum distillation was carried out at 70° C. and 10.7 to 13.3 kPa (80 to 100 Torr). The results are shown in Table 2.

In Table 2, "-" indicates the case in which detection or quantification was difficult or impossible.

TABLE 1

| Ex | Reverse Diffusion/ Initial Permeation Velocity (flux) | Linear Velocity [cm/s] | Operating Temperature [° C.] | Pressure [kPa] | Average Thickness Variation Coefficient [%] | Initial Permeation Flux [L/(m² × hr)] |
|---|---|---|---|---|---|---|
| 1 | 0.02 | 3.3 | 25 | — | 30 | 7 |
| 2 | 0.015 | 3.3 | 25 | — | 30 | 4 |
| 3 | 0.005 | 3.3 | 25 | 100 | 30 | 5 |
| 4 | 0.006 | 3.3 | 25 | — | 30 | 7 |
| 5 | 0.001 | 3.3 | 25 | 100 | 30 | 8 |
| 6 | 0.013 | 3.3 | 25 | 10 | 30 | 5 |
| 7 | 0.009 | 3.3 | 25 | 200 | 30 | 6 |
| 8 | 1 | 3.3 | 25 | — | 30 | 9 |
| 9 | 3 | 3.3 | 25 | — | 30 | 10 |
| 10 | 5 | 3.3 | 25 | — | 30 | 15 |
| 11 | 0.02 | 20 | 25 | — | 30 | 10 |
| 12 | 0.03 | 0.02 | 25 | — | 30 | 5 |
| 13 | 0.02 | 15 | 25 | — | 30 | 10 |
| 14 | 0.03 | 0.03 | 25 | — | 30 | 5 |
| 15 | 0.03 | 3.3 | 50 | — | 30 | 10 |
| 16 | 0.013 | 3.3 | 5 | — | 30 | 3 |
| 17 | 0.02 | 3.3 | 25 | — | 30 | 3 |
| 18 | 0.01 | 3.3 | 25 | — | 30 | 5 |
| 19 | 0.03 | 3.3 | 25 | — | 30 | 9 |
| 20 | 0.02 | 3.3 | 25 | — | 30 | 7 |
| 21 | 0.02 | 3.3 | 25 | — | 30 | 8 |
| 22 | 0.02 | 3.3 | 25 | — | 30 | 7 |
| 23 | 0.02 | 3.3 | 25 | — | 30 | 6 |
| 24 | 0.02 | 3.3 | 25 | — | 30 | 7 |
| 25 | 0.02 | 3.3 | 25 | — | 30 | 8 |
| 26 | 0.02 | 3.3 | 25 | — | 30 | 5 |
| 27 | 0.03 | 3.3 | 25 | — | 30 | 7 |
| 28 | 0 | 3.3 | 25 | — | 30 | 2 |

| Ex | Recovery Rate [%] | Purity [%] | Resin | Solute | DS (draw solvent) | Solvent |
|---|---|---|---|---|---|---|
| 1 | A | A | PES | alanyl glutamine | 20% magnesium chloride aqueous solution | acetonitrile (15 wt %) |
| 2 | A | A | PES | alanyl glutamine | 10% magnesium chloride aqueous solution | acetonitrile (15 wt %) |
| 3 | A | A | PES | alanyl glutamine | 10% magnesium chloride aqueous solution | acetonitrile (15 wt %) |
| 4 | A | A | PES | alanyl glutamine | 10% magnesium chloride aqueous solution | water |
| 5 | A | A | PES | alanyl glutamine | 10% magnesium chloride aqueous solution | water |
| 6 | A | A | PES | alanyl glutamine | 10% magnesium chloride aqueous solution | acetonitrile (15 wt %) |
| 7 | A | A | PES | alanyl glutamine | 10% magnesium chloride aqueous solution | acetonitrile (15 wt %) |
| 8 | A | A | PES | alanyl glutamine | 20% magnesium chloride aqueous solution | acetonitrile (15 wt %) |

TABLE 1-continued

| | | | | | | |
|---|---|---|---|---|---|---|
| 9 | A | B | PES | alanyl glutamine | 20% magnesium chloride aqueous solution | acetonitrile (15 wt %) |
| 10 | A | C | PES | alanyl glutamine | 20% magnesium chloride aqueous solution | acetonitrile (15 wt %) |
| 11 | B | A | PES | alanyl glutamine | 20% magnesium chloride aqueous solution | acetonitrile (15 wt %) |
| 12 | B | A | PES | alanyl glutamine | 20% magnesium chloride aqueous solution | acetonitrile (15 wt %) |
| 13 | A | A | PES | alanyl glutamine | 20% magnesium chloride aqueous solution | acetonitrile (15 wt %) |
| 14 | A | A | PES | alanyl glutamine | 20% magnesium chloride aqueous solution | acetonitrile (15 wt %) |
| 15 | A | A | PES | alanyl glutamine | 20% magnesium chloride aqueous solution | acetonitrile (15 wt %) |
| 16 | A | A | PES | alanyl glutamine | 20% magnesium chloride aqueous solution | acetonitrile (15 wt %) |
| 17 | A | A | PS | alanyl glutamine | 10% magnesium chloride aqueous solution | acetonitrile (15 wt %) |
| 18 | A | A | PK | alanyl glutamine | 10% magnesium chloride aqueous solution | acetonitrile (15 wt %) |
| 19 | A | A | PES | alanyl glutamine | 20% magnesium chloride aqueous solution | methanol(10 wt %) |
| 20 | A | A | PES | alanyl glutamine | 20% magnesium chloride aqueous solution | 2-propanol (10 wt %) |
| 21 | A | A | PES | olegonucleotide | 20% magnesium chloride aqueous solution | acetonitrile (15 wt %) |
| 22 | A | A | PES | asparagine | 20% magnesium chloride aqueous solution | acetonitrile (15 wt %) |
| 23 | A | A | PES | streptomycin | 20% magnesium chloride aqueous solution | acetonitrile (15 wt %) |
| 24 | A | A | PES | mitomycin C | 20% magnesium chloride aqueous solution | acetonitrile (15 wt %) |

TABLE 1-continued

| | | | | | | |
|---|---|---|---|---|---|---|
| 25 | A | A | PES | vitamin A | 20% magnesium chloride aqueous solution | acetonitrile (15 wt %) |
| 26 | A | A | PES | alanyl glutamine | 25% magnesium sulfate aqueous solution | acetonitrile (15 wt %) |
| 27 | A | A | PES | alanyl glutamine | 20% sodium chloride aqueous solution | acetonitrile (15 wt %) |
| 28 | B | A | PES | alanyl glutamine | 50% sucrose | acetonitrile (15 wt %) |

TABLE 2

| Comp Ex | Linear Velocity [cm/s] | Operating Temperature [° C.] | Initial Permeation Flux [L/(m² × hr)] | Recovery Rate [%] | Resin | Solute | Solvent |
|---|---|---|---|---|---|---|---|
| 1 | 100 | 25 | 100 | D | PES | alanyl glutamine | acetonitrile (15 wt %) |
| 2 | 10 | 25 | 30 | D | PES | alanyl glutamine | acetonitrile (15 wt %) |
| 3 | — | 70 | — | D | — | alanyl glutamine | acetonitrile (15 wt %) |

REFERENCE SIGNS LIST

100, 200, 300, 400, 500 raw material liquid concentration system
11 forward osmosis membrane unit
21 circulation mechanism
31 first draw solution regeneration unit
41 second draw solution regeneration unit
42 mixing unit
a raw material liquid
b solvent
c concentrated raw material liquid
d draw solution
e diluted draw solution
f regenerated draw solution
g concentrated draw solution
forward osmosis membrane
s draw substance
r draw solution reverse diffusion
D draw solution-side space
R raw material liquid-side space

The invention claimed is:

1. A raw material liquid concentration method for a pharmaceutical production process, the method having:
a first step wherein a raw material liquid containing a solvent and a solute and a draw solution containing a draw substance are contacted via a forward osmosis membrane to move the solvent in the raw material liquid into the draw solution and move the draw substance in the draw solution into the raw material liquid to obtain a concentrated raw material liquid and a diluted draw solution, wherein a ratio (permeation flux of the draw substance [g/(m²×hr)]/permeation flux of the solvent [L/m²×hr)]) of a permeation flux of the draw substance, by which the draw substance in the draw solution is moved into the raw material liquid, to a permeation flux of the solvent, by which the solvent in the raw material liquid is moved into the draw solution, in the first step is 3 [g/L] or less.

2. The raw material liquid concentration method according to claim 1, wherein the forward osmosis membrane is a hollow fiber membrane.

3. The raw material liquid concentration method according to claim 2, wherein
a plurality of the hollow fiber membranes form a hollow-fiber fiber bundle,
the hollow fiber membranes each comprise a microporous support membrane and a separation active layer, which is a polymer thin film provided on an inner surface of the microporous support membrane,
a membrane area of the hollow-fiber fiber bundle is 0.01 m² or more, and
a coefficient of variation of a thickness of the separation active layer in the radial direction and the longitudinal direction of the hollow-fiber fiber bundle in a scanning electron microscope image in which a thickness-direction cross-section of the separation active layer is captured, is 0 to 60%.

4. The raw material liquid concentration method according to claim 2, wherein in the first step, a pressure of 10 kPa to 200 kPa is exerted from an interior toward an exterior of the hollow fiber membrane.

5. The raw material liquid concentration method according to claim 1, wherein in the first step, the temperature of the raw material liquid is adjusted to the range of 5° C. to 50° C.

6. The raw material liquid concentration method according to claim 1, further having a draw solution regeneration step wherein the solvent is removed from the diluted draw solution to obtain a regenerated draw solution and the obtained regenerated draw solution is used again as the draw solution.

7. The raw material liquid concentration method according to claim 1, further having a draw solution regeneration step wherein the solvent is removed from the draw solution to obtain a concentrated draw solution and a mixture of the obtained concentrated draw solution and the diluted draw solution is used as the draw solution.

8. The raw material liquid concentration method according to claim 1, wherein the forward osmosis membrane is a membrane having a thin film layer composed of at least one selected from the group consisting of polyethersulfone, polysulfone, polyketone, polyetheretherketone, polyphenylene ether, polyvinylidene fluoride, polyacrylonitrile, polyimine, polyimide, polybenzoxazole, polybenzimidazole, sulfonated tetrafluoroethylene, and polyamide as primary components.

9. The raw material liquid concentration method according to claim 1, wherein a ratio (permeation flux of the draw substance [g/(m²×hr)]/permeation flux of the solvent) [L/m²×hr)]) of a permeation flux of the draw substance, by which the draw substance in the draw solution is moved into the raw material liquid, to a permeation flux of the solvent, by which the solvent in the raw material liquid is moved into the draw solution, in the first step is 0.001 to 1 [g/L].

10. The raw material liquid concentration method according to claim 1, wherein the solvent is composed of water, acetic acid, acetonitrile, methanol, 2-propanol or mixtures thereof as primary components.

11. The raw material liquid concentration method according to claim 1,
wherein in the first step, the concentrated raw material liquid is circulated through a circulation mechanism at a circulation linear velocity of 0.03 cm/s to 15 cm/s, the circulation linear velocity being calculated by the following formula

X=Y/Z where X is a linear velocity of the concentrated raw material liquid in the circulation mechanism [cm/s], Y is a flow velocity of the concentrated raw material liquid in the circulation mechanism [cm³/s], and Z is a total hollow fiber inner cross-sectional area [cm²].

12. The raw material liquid concentration method according to claim 1, wherein the pharmaceutical production process is a process for the production of at least one selected from the group consisting of nucleic acids, oligopeptides, amino acids, antibiotics, small molecule pharmaceuticals, and vitamins.

13. The raw material liquid concentration method according to claim 1, wherein the solute comprises a compound having a number average molecular weight of 100 to 6000.

* * * * *